United States Patent [19]

Arndts et al.

[11] Patent Number: 5,677,304

[45] Date of Patent: Oct. 14, 1997

[54] 9-AMINO-PYRIDAZINO[4'5':3,4]PYRROLO-[2,1-A]ISOQUINOLINES AND THE USE THEREOF FOR THE PRODUCTION OF PHARMACEUTICAL PREPARATIONS

[75] Inventors: Dietrich Arndts, Appenheim; Walter Lösel, Gau-Algesheim; Otto Roos, Schwabenheim, all of Germany

[73] Assignee: Boehringer Ingelheim KG, Ingelheim am Rhein, Germany

[21] Appl. No.: 649,550

[22] Filed: May 17, 1996

Related U.S. Application Data

[62] Division of Ser. No. 334,979, Nov. 7, 1994, Pat. No. 5,565,452, which is a continuation of Ser. No. 81,916, Jun. 22, 1993, abandoned.

[30] Foreign Application Priority Data

| Jun. 22, 1992 | [DE] | Germany | 42 20 384.8 |
| Jun. 22, 1992 | [DE] | Germany | 42 20 361.9 |
| Jun. 22, 1992 | [DE] | Germany | 42 20 380.5 |

[51] Int. Cl.$^6$ .............................................. A61K 31/495
[52] U.S. Cl. .................................. 514/248; 544/233
[58] Field of Search ........................ 514/248; 544/233

[56] References Cited

PUBLICATIONS

Loesel et al, Chem. Abst., vol. 105, # 172,490n (1986).
Loesel et al, Chem. Abst., vol. 106, # 102,310a (1987).
Loesel et al, Chem. Abst., vol. 109, # 204,921e (1988).

*Primary Examiner*—James H. Reamer
*Attorney, Agent, or Firm*—Robert P. Raymond; Wendy E. Rieder; Alan R. Stempel

[57] ABSTRACT

The invention relates to the use of 9-amino-pyridazino-[4', 5':3,4]pyrrolo[2,1-a]isoquinolines of the formula

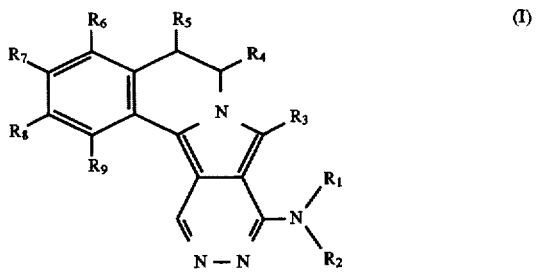

and the physiologically acceptable salts thereof with acids, bases and complexing agents for preparing agents for treating chronic inflammatory processes, ulcerative colitis and Crohn's disease, and for producing agents having an antiproliferative activity. The definitions of substituents $R_1$ to $R_9$ are given in the specification. The invention also relates to new compounds of general formula I which are also defined in the specification and their use as cerebroprotective agents.

30 Claims, No Drawings

9-AMINO-PYRIDAZINO[4'5':3,4]PYRROLO-[2,1-A]ISOQUINOLINES AND THE USE THEREOF FOR THE PRODUCTION OF PHARMACEUTICAL PREPARATIONS

This is a division of application Ser. No. 08/334,979, filed Nov. 7, 1994, now U.S. Pat. No. 5,565,452, which is a continuation of application Ser. No. 08/081,916, filed Jun. 22, 1993, now abandoned.

The invention relates to the use of 9-amino-pyridazino [4',5':3,4]pyrrolo[2,1-a]isoquinolines of the formula

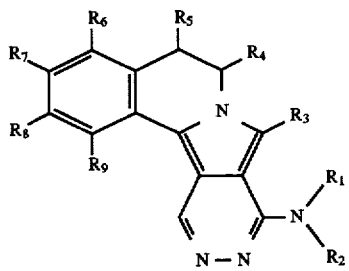

(Ia)

and the physiologically acceptable salts thereof with acids, bases and complex-forming agents for preparing agents for treating chronic inflammatory processes, ulcerative colitis and Crohn's disease and for producing agents having an antiproliferative effect.

As explained hereinafter, some of these compounds are known from DE 35 00 941, DE 35 25 048, EP 190 563 and EP 252 299; some of the compounds, however, are new. The present invention therefore also relates to these new compounds, pharmaceutical preparations containing these compounds, particularly the use thereof as cerebroprotective agents, particularly in the treatment of patients who have suffered a stroke or are in danger of suffering a stroke.

In formula Ia:

$R_1$ and $R_2$, which may be identical or different, denote hydrogen; $C_{3-7}$-cycloalkyl; $C_{2-5}$-alkenyl; phenyl (wherein the phenyl ring may optionally be mono- or disubstituted by halogen or methoxy); propargyl; a straight-chained or branched, saturated or unsaturated $C_{1-5}$-alkyl group, which may be substituted by hydroxy, $C_{1-4}$-alkoxy, halogen, $NH_2$, NH-alkyl having 1 to 2 carbon atoms, N,N-di($C_{1-2}$) alkylamino, NH-acyl having 2 to 4 carbon atoms, $C_{3-7}$-cycloalkyl, 1 or 2 phenyl groups, wherein the phenyl ring or rings may in turn be mono- or disubstituted by halogen, $CF_3$, $C_{1-4}$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms, alkylsulphonylamino or benzyloxy), furyl, thienyl, a nitrogen-containing heterocyclic 5- or 6-membered ring which may optionally contain as a further heteroatom an oxygen or sulphur atom (whilst the ring may optionally be substituted by $C_{1-4}$-alkyl); or $R_1$ and $R_2$ together with the nitrogen atom denote a 3- to 7-membered ring which may optionally contain, as a further heteroatom, an oxygen or nitrogen atom, whilst this ring is optionally substituted by phenyl-($C_{0-4}$)-alkyl (whilst the phenyl ring may in turn be mono- or disubstituted by halogen, $CF_3$, ($C_{1-4}$)alkoxy, ($C_{1-4}$)alkyl or CN, whilst the substituents may be identical or different); or if $R_1$ denotes hydrogen, $R_2$ may also represent -$NH_2$; di($C_{1-2}$)alkylamino; acetonylamino; —NH($C_{2-3}$)acyl; an alkylsulphonyl or alkoxycarbonyl group having 1 to 3 carbon atoms in the alkyl chain; the isopropylideneamino group

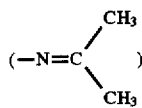

or a heterocyclic 5- or 6-membered ring containing a nitrogen atom and optionally an oxygen, nitrogen or sulphur atom as a further heteroatom;

$R_3$, $R_4$ and $R_5$, which may be identical or different denote hydrogen or a $C_{1-4}$-alkyl group;

$R_7$ and $R_8$, which may be identical or different, represent hydroxy; $C_{1-4}$-alkoxy; or $C_{1-4}$-alkylthio and $R_6$ and $R_9$, which may be identical or different, denote hydrogen; hydroxy; $C_{1-4}$-alkoxy; $C_{1-4}$-alkylthio; or the group

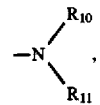

wherein $R_{10}$ denotes hydrogen; or $C_{1-4}$-alkyl and $R_{11}$ denotes hydrogen; or $C_{1-4}$-alkyl, whilst the alkyl group may optionally be substituted by hydroxy, methoxy or furfuryl;

or 2 adjacent substituents of the substituents $R_6$, $R_7$, $R_8$ and $R_9$ together form the group —O—$(CH_2)_{1\,or\,2}$—O— and the other two substituents are as hereinbefore defined.

The invention further relates to the use of the physiologically acceptable salts thereof with acids, bases or complexing agents in order to prepare agents for treating chronic inflammatory processes, ulcerative colitis and Crohn's disease, and agents having an antiproliferative effect.

Preferred for use according to the invention include a compound of formula (Ia) (as defined above) wherein $R_1$ and $R_2$, which may be identical or different, represent hydrogen; $C_{3-7}$-cycloalkyl; $C_{2-5}$-alkenyl; phenyl (wherein the phenyl ring is optionally mono- or disubstituted by halogen or methoxy); propargyl; a straight-chained or branched, saturated or unsaturated $C_{1-5}$-alkyl group which may be substituted by hydroxy, $C_{1-4}$-alkoxy, halogen, $NH_2$, NH-alkyl having 1 to 2 carbon atoms, N,N-di($C_{1-2}$) alkylamino, NH-acyl having 2 to 4 carbon atoms, $C_{3-7}$-cycloalkyl, phenyl (whilst the phenyl ring may in turn be mono- or disubstituted by halogen, $C_{1-2}$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms or alkylsulphonylamino), furyl, thienyl, a nitrogen-containing heterocyclic 5- or 6-membered ring which may optionally contain an oxygen or sulphur atom as a further heteroatom (whilst the ring is optionally substituted by $C_{1-4}$-alkyl); or $R_1$ and $R_2$ together with the nitrogen atom denote a 3- to 7-membered ring which may optionally contain an oxygen or nitrogen atom as a further heteroatom, whilst this ring is optionally substituted by phenyl-($C_{0-4}$)alkyl (whilst the phenyl ring is in turn mono- or disubstituted by halogen or methoxy); or $R_2$, if $R_1$ denotes hydrogen, may also denote —$NH_2$; di($C_{1-2}$)alkylamino; acetonylamino; —NH($C_{2-3}$)acyl; an alkylsulphonyl or alkoxycarbonyl group each having 1 to 3 carbon atoms in the alkyl chain; the isopropylideneamino group

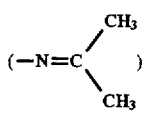

or a heterocyclic 5- or 6-membered ring containing a nitrogen atom and optionally, as a further heteroatom, an oxygen, nitrogen or sulphur atom;

$R_3$, $R_4$ and $R_5$, which may be identical or different, denote hydrogen or a $C_{1-4}$-alkyl group;

$R_7$ and $R_8$, which may be identical or different, denote hydroxy; $C_{1-4}$-alkoxy; or $C_{1-4}$-alkylthio and $R_6$ and $R_9$, which may be identical or different, denote hydrogen; hydroxy; $C_{1-4}$-alkoxy; $C_{1-4}$-alkylthio; or the group

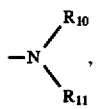

wherein $R_{10}$ denotes hydrogen; or $C_{1-4}$-alkyl and $R_{11}$ denotes hydrogen; or $C_{1-4}$-alkyl, whilst the alkyl group may optionally be substituted by hydroxy, methoxy or furfuryl;

and the physiologically acceptable salts thereof with acids, bases or complexing agents for preparing agents for treating chronic inflammatory processes, ulcerative colitis and Crohn's disease, and for producing agents with an antiproliferative activity.

a compound of formula (Ia) wherein
—$NR_1R_2$ represents

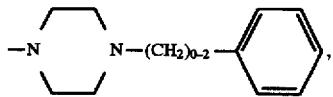

wherein the phenyl group may be substituted by one or two methoxy groups.

a compound of formula (Ia) wherein —$NR_1R_2$ denotes the group

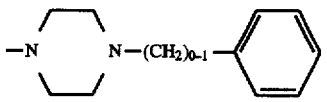

wherein the phenyl group may be substituted as defined hereinbefore.

a compound of formula (Ia) wherein —$NR_1R_2$ denotes the group

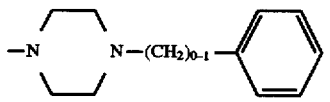

wherein the phenyl ring is mono- or disubstituted by fluorine, chlorine, $CF_3$, methoxy, methyl, ethyl or CN.

a compound of formula (Ia) wherein $R_1$ is hydrogen and $R_2$ is a straight-chained or branched $C_{1-4}$-alkyl group which is substituted by $C_{3-7}$-cycloalkyl, thienyl or 1 or 2 unsubstituted phenyl groups or a substituted phenyl group the substituent(s) of which is or are defined as hereinbefore.

a compound of formula (Ia) wherein $R_1$ is hydrogen and $R_2$ is ($C_{1-4}$)alkylcyclohexyl, preferably —$CH_2$-$C_6H_{11}$.

a compound of formula (Ia) wherein $R_1$ is hydrogen and $R_2$ is ($C_{1-4}$)alkylphenyl, wherein the phenyl group is unsubstituted or mono- or disubstituted by F, Cl, $CF_3$, methyl, ethyl, methoxy or ethoxy.

a compound of formula (Ia) wherein $NR_1R_2$ is one of the following groups:

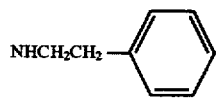

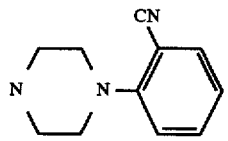

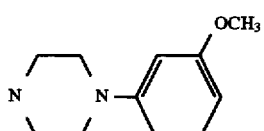

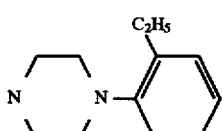

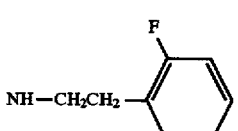

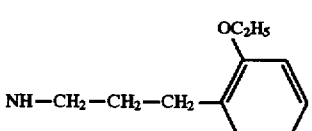

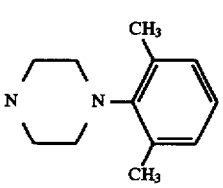

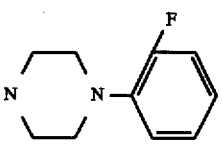

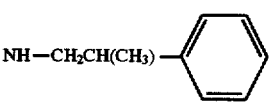

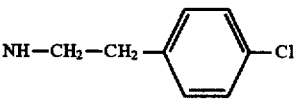

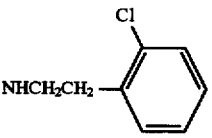

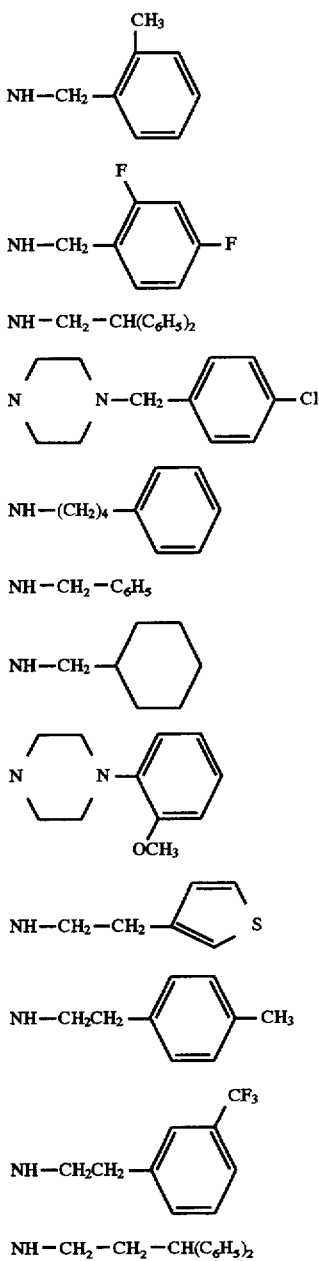

a compound of formula (Ia) wherein $NR_1R_2$ is one of the following groups:

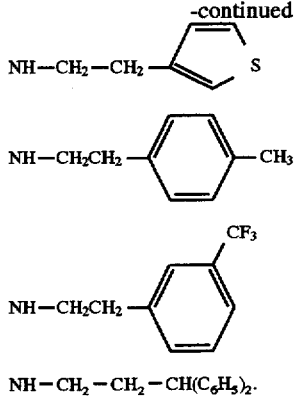

a compound of formula (Ia) wherein $R_3$, $R_4$, $R_5$, $R_6$ and $R_9$ denote hydrogen and $R_7$ and $R_8$ represent $C_{1-4}$-alkoxy or $R_7$ and $R_8$ together represent —$OCH_2O$— or —$OCH_2CH_2O$—.

a compound of formula (Ia) wherein $R_7$ and $R_8$ are methoxy.

It is also preferable to use those compounds of general formula Ia wherein $R_1$ and $R_2$, which may be identical or different, denote hydrogen; a straight-chained or branched $C_{1-5}$-alkyl group or $R_1$ denotes hydrogen and $R_2$ denotes amino; methylamino; dimethylamino; isopropylideneamino; dimethylamino-$C_{1-4}$-alkyl; methoxy-$C_{1-4}$-alkyl; cyclopropyl; cyclopentyl; cyclohexyl; cyclohexylmethyl; phenyl; phenylethyl, wherein the phenyl ring is optionally mono- or disubstituted by methoxy or halogen; pyrazolyl; propargyl; [1-methylpyrrolidin-2-yl]-ethyl; (piperidin-1-yl)ethyl; allyl; 4-benzyl-piperazin-l-yl; (furan-2-yl)methyl; (pyrrolidin-1-yl)-ethyl; 2-hydroxyethyl; (pyridin-4-yl)-ethyl; benzyl; (thien-3-yl)-ethyl; or $R_1$ and $R_2$ together with the nitrogen atom to which they are bound denote pyrrolidine; morpholine; piperazine which may optionally be substituted by phenethyl or methoxyphenyl;

and $R_7$ and $R_8$ independently of each other denote hydrogen; methyl; methoxy; hydroxy; or methylthio and $R_3$, $R_4$, $R_5$, $R_6$ and $R_9$ denote hydrogen.

The compounds of formula Ia are bases and may be converted in the usual way with inorganic or organic acids and salt and complex-forming agents into any desired physiologically harmless adducts (salts).

Acids suitable for salt formation include, for example, hydrochloric acid, hydrobromic acid, hydriodic acid, hydrofluoric acid, sulphuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, phthalic acid, cinnamic acid, salicylic acid, ascorbic acid, methanesulphonic acid and the like.

It is preferable to use compounds of general formula Ia wherein $R_3$, $R_4$, $R_5$, $R_6$ and $R_9$ denote hydrogen and $R_7$ and $R_8$ denote methoxy, and/or $R_1$ is hydrogen and $R_2$ is a group —$(CH_2)_{0-3}$-A, wherein A denotes cyclopentyl, cyclohexyl, phenyl, mono- or dimethoxyphenyl

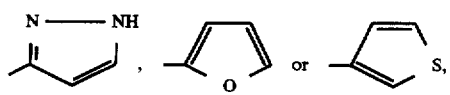

or $R_2$ is branched or unbranched $C_{4-5}$-alkyl; particularly compounds wherein the group

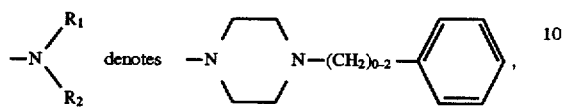

wherein the phenyl group may be substituted by one or two methoxy groups; or $R_1$ is hydrogen and $R_2$ is one of the following groups cyclopentyl
cyclohexyl
phenyl

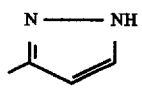

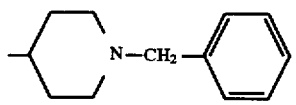

—CH$_2$—C$_6$H$_5$

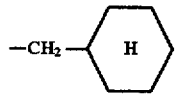

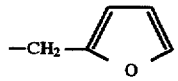

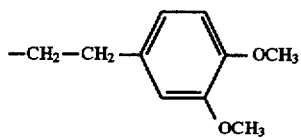

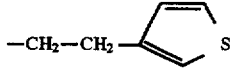

—(CH$_2$)$_3$CH$_3$
—(CH$_2$)$_4$CH$_3$
—CH$_2$—CH(CH$_3$)$_2$
—(CH$_2$)$_2$—CH(CH$_3$)$_2$
—(CH$_2$)$_3$—OCH$_3$ or the group

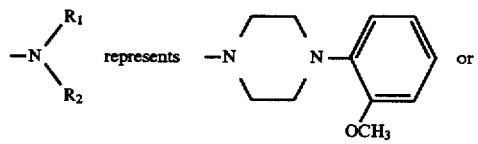

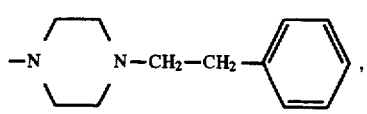

more particularly wherein $R_1$ is hydrogen and $R_2$ is one of the following groups

—CH$_2$—C$_6$H$_5$

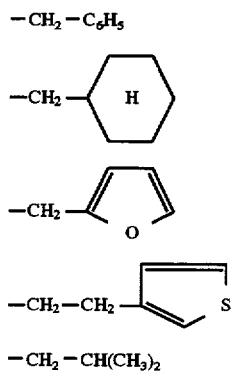

—CH$_2$—CH(CH$_3$)$_2$ or the group

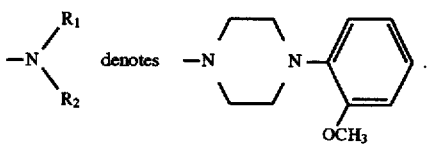

Tables 1 and 2 which follow list examples of compounds of formula Ia.

The compounds in Table 1 are known from the publications DE 35 00 941, DE 35 25 048, EP 190 563 and EP 252 299 mentioned earlier.

The compounds in Table 2 are examples of the new compounds of general formula Ia.

TABLE 1

| | Salt form |
|---|---|
| NH—CH$_2$CH$_2$—N(CH$_3$)$_2$ | HCl |
| NH—NH$_2$ | HCl |
| N(CH$_3$)$_2$ | HCl |
| NH$_2$ | Base |
| NHCH$_3$ | HCl |
| NHC$_2$H$_5$ | HCl |
| N(C$_2$H$_5$)$_2$ | HCl |
| NH—▷ | HCl |
| ⟨N O⟩ | HCl |
| NH—CH$_2$—CH(CH$_3$)$_2$ | HCl |
| NH—CH$_2$—C$_6$H$_5$ | HCl |
| NH—CH(CH$_3$)$_2$ | HCl |
| NH—CH$_2$—CH$_2$—CH$_2$—CH$_3$ | HCl |
| NH—N(CH$_3$)$_2$ | HCl |
| NH—CH$_2$—CH$_2$—OCH$_3$ | HCl or HI |

TABLE 1-continued
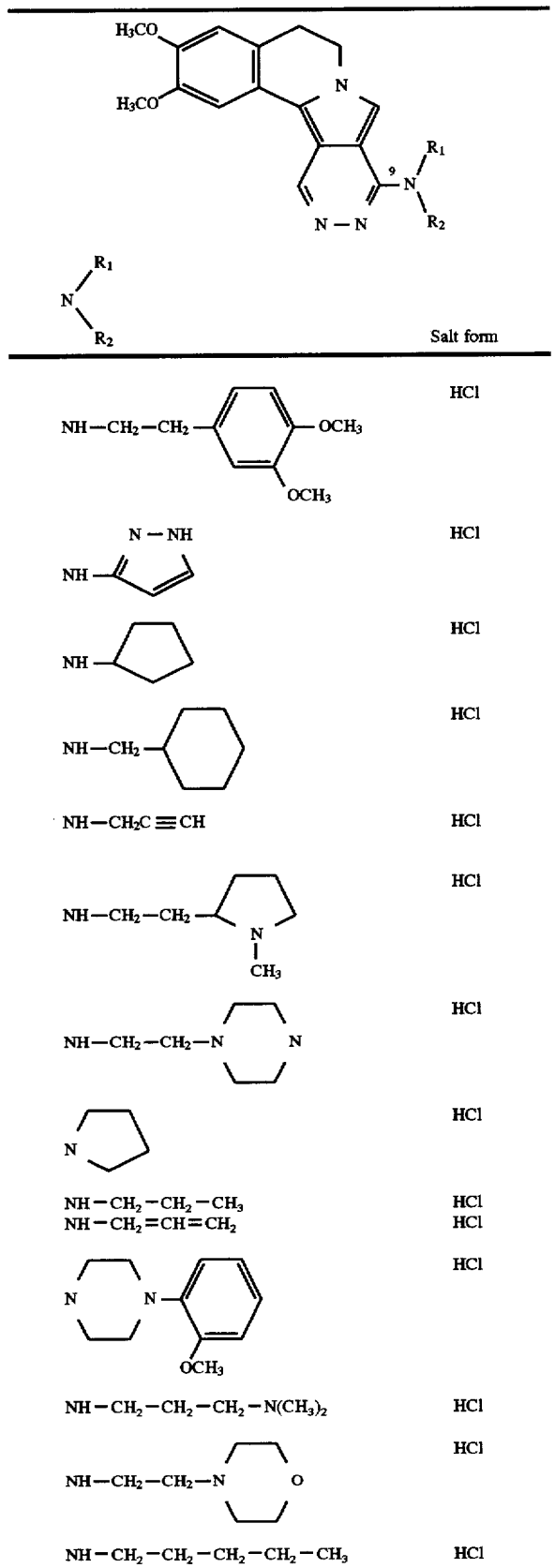
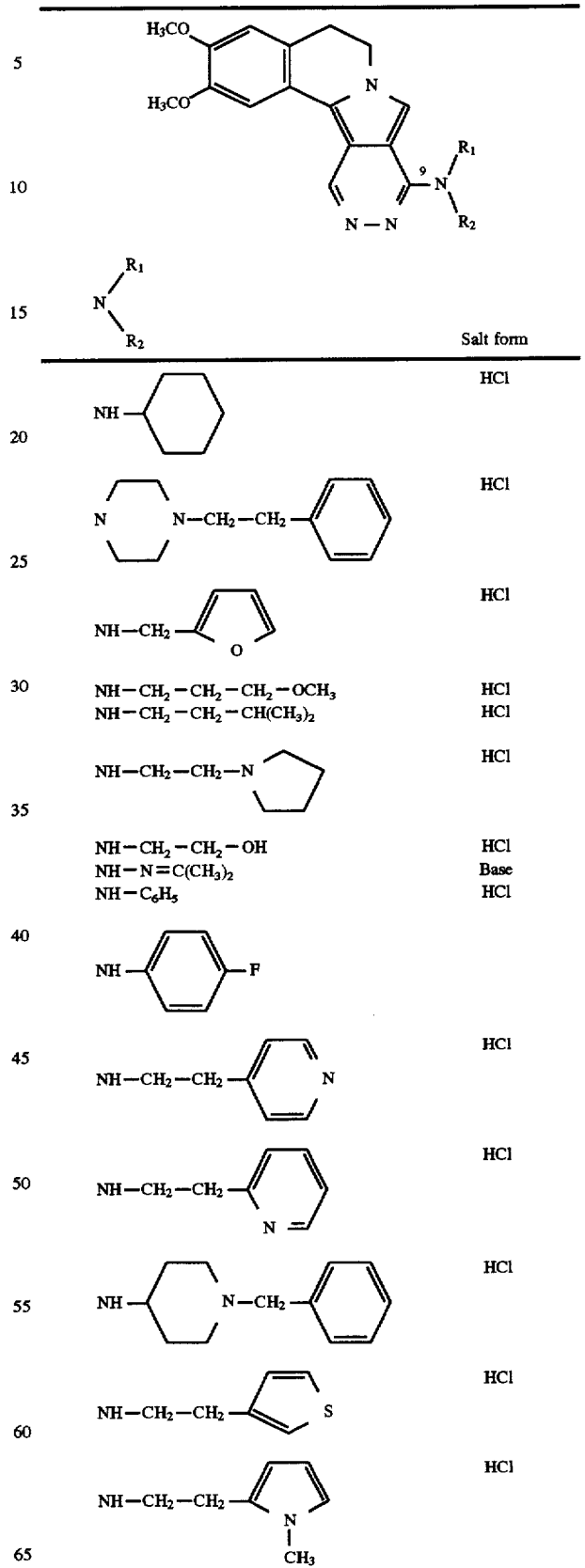

TABLE 1-continued

[Structure: 8,9-dimethoxy-pyrrolo-isoquinoline with pyridazine bearing NR₁R₂ substituent]

| −N(R₁)(R₂) | Salt form |
|---|---|
| NH−CH₂−CH₂−N(piperidine) | HCl |

TABLE 2

[Structure: 8,9-dimethoxy-pyrrolo-isoquinoline with pyridazine bearing NR₁R₂ substituent · HCl]

| −N(R¹)(R²) | M.p. °C. |
|---|---|
| NH−CH₂CH₂−C₆H₄−CH₃ (p-) | 270–272 |
| NHCH₂CH₂−C₆H₅ | 274–275 |
| piperazine−C₆H₄(o-CN) | 291 |
| piperazine−C₆H₄(m-OCH₃) | 266–268 |
| NH−CH₂−CH₂−CH₂−C₆H₄(m-CH₃) | 243–245 |

TABLE 2-continued

[Structure: 8,9-dimethoxy-pyrrolo-isoquinoline with pyridazine bearing NR₁R₂ substituent · HCl]

| −N(R¹)(R²) | M.p. °C. |
|---|---|
| piperazine−C₆H₄(o-C₂H₅) | 305 |
| NH−CH₂CH₂−C₆H₄(o-F) | 268–269 |
| NH−CH₂CH₂−C₆H₄(m-CF₃) | 264–266 |
| NH−CH₂−CH₂−(2-thienyl) | 277 |
| NH−CH₂−CH₂−CH₂−C₆H₃(2,5-di-OCH₃) | 210–211 |
| NH−CH₂−CH₂−CH₂−C₆H₄(o-OC₂H₅) | 269–270 |
| piperazine−C₆H₃(2,6-di-CH₃) | 294–295 |
| piperazine−C₆H₄(o-F) | 295 |

TABLE 2-continued

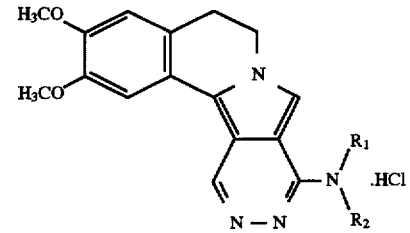

| −N(R¹)(R²) | M.p. °C. |
|---|---|
| 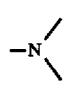 | 289–290 |
| NH—CH₂CH(CH₃)—C₆H₅ | 252–253 |
| NH—CH₂—CH₂—CH₂—C₆H₄—F (4-F) | 250–251 |
| NH—CH₂—CH₂—C₆H₄—Cl (4-Cl) | 293–295 |
| NHCH₂CH₂—C₆H₄—Cl (2-Cl) | 266–267 |
| NH—CH₂—C₆H₄—OC₂H₅ (2-OC₂H₅) | 176–178 |
| NH—CH₂—C₆H₄—CF₃ (2-CF₃) | 289–290 |
| NH—CH₂—C₆H₄—F (2-F) | 272–273 |
| NH—CH₂—CH₂—C₆H₄—F (3-F) | 278 |
| NH—CH₂—CH₂—CH₂—C₆H₅ | 253–254 |

TABLE 2-continued

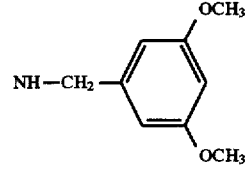

| −N(R¹)(R²) | M.p. °C. |
|---|---|
| NH—CH₂—C₆H₃(OCH₃)₂ (3,5-diOCH₃) | 255 |
| NH—CH₂CH₂—C₆H₄—C(CH₃)₃ (4-tBu) | 269–270 |
| NH—CH₂—C₆H₃(OCH₃)₂ (2,4-diOCH₃) | 241–243 |
| NH—CH₂—C₆H₄—CH₃ (2-CH₃) | 268–269 |
| NH—CH₂—CH₂—CH(C₆H₅)₂ | 180–182 |
| N(CH₃)CH₂CH₂—C₆H₃(OCH₃)₂ (3,4-diOCH₃) | 244 |
| 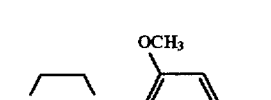 | 284–285 |
| NH—CH₂—CH₂—C₆H₁₁ (cyclohexyl) | 281–282 |
|  | 262–263 |

TABLE 2-continued

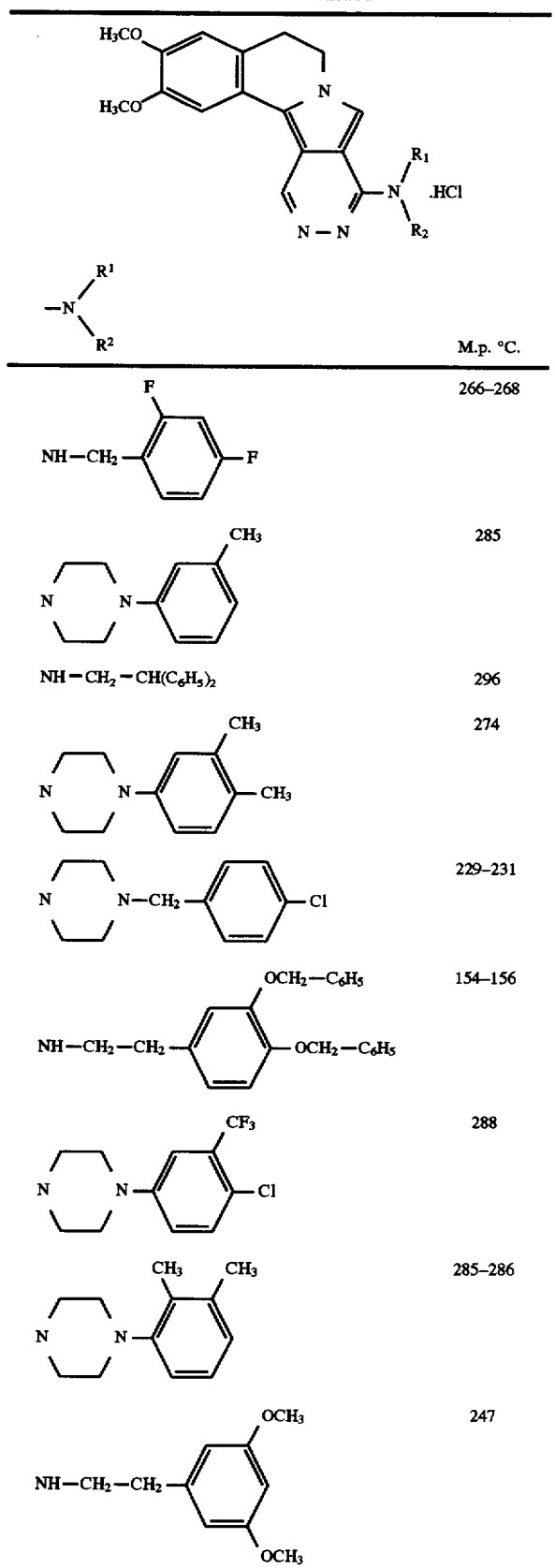

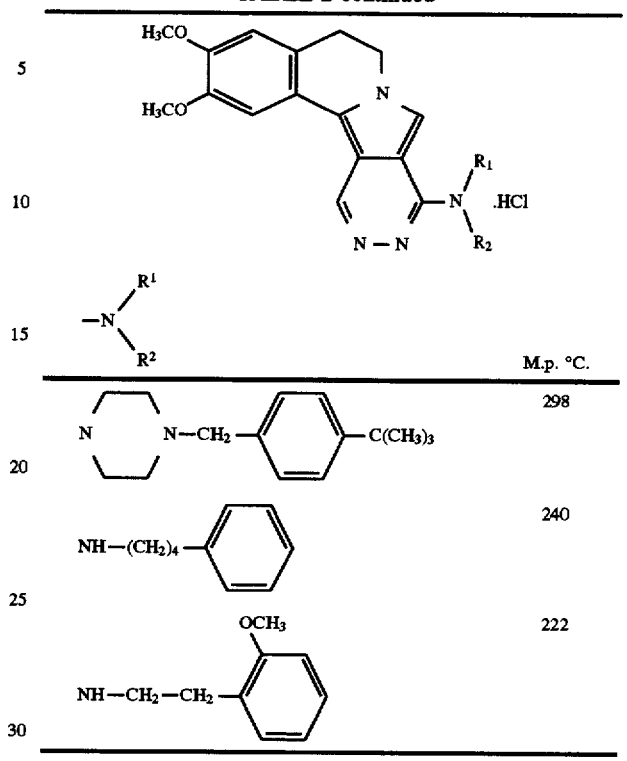

Cardiotonically active compounds of general formula Ia are known from German Patent Applications DE 35 00 941.1, DE 35 25 048.8 and European Patent 190 563. According to these applications, these compounds may be used to combat cardiac insufficiency and/or cerebral metabolic disorders. From European Patent Application No. 252 299 (A) it is known that these compounds have a cardioprotective and neuroprotective activity and they further promote circulation through the tissues and the supply of oxygen to the tissues in the central nervous system.

One aspect of the present invention consists of the new compounds mentioned hereinbefore and pharmaceutical preparations containing these compounds. The present invention further relates to the use of these new compounds. The compounds are beneficial for treating degenerative and necrotic diseases of the brain. It is also possible to use them as preventative treatment for patients at risk of such diseases. This activity of the compounds is not based on an improvement in blood flow to the tissues. Thus, the compounds are suitable for a new kind of treatment for epilepsy and Alzheimer's disease and particularly for treating patients who have suffered a stroke or in danger of suffering a stroke.

The present invention also relates to the use of the above-mentioned old and new compounds of general formula Ia and the salts thereof for the production of agents for treating chronic inflammatory processes, ulcerative colitis and Crohn's disease and for producing agents having an antiproliferative effect. The activity of the compounds can be explained by their inhibition of the unselective cation channels (UCC).

The pathophysiology of chronic bronchial asthma is based on inflammatory processes which are mediated by the activation of inflammatory cells. (BARNES, 1987; SEIFERT and SCHULTZ, 1991).

The receptor-regulated activation of inflammatory cells (e.g. neutrophilic granulocytes and mast cells or the permanent cell lines HL-60 cells or sensitised RBL cells, i.e. those charged with gammaglobulin E) is inhibited, irrespective of the nature of the stimulating agonists (e.g. endothelin, PAF, leukotrienes, chemotactical peptide fMLP or antigen against sensitised mast cells) by blockers of unselective cation channels (UCC) (RINK, 1990). Through these channels extracellular calcium, which is responsible for the persistence of receptor-mediated cell activations, enters the cells (PUTNEY, 1990). If this supply of calcium is interrupted this results in a blockade of the activation of inflammatory cells.

Conventional calcium antagonists of the dihydropyridine or phenylalkylamine type do not inhibit either UCCs or inflammatory processes (WELLS et al., 1986).

As a measurement of the cell activation or as a measurement of the inhibition thereof by UCC blockers, the kinetics of the cytoplasmic calcium ion concentration in fura-2-charged cells is quantified fluorometrically using the method described by GRYNKIEWICZ et al. (1985). This procedure has proved a reliable screening method, within the scope of the invention, for detecting UCC blockers.

So-called functional THAPSIGARGIN inhibition has proved suitable for the specific characterisation of blockers of the unselective cation channels. THAPSIGARGIN is a tumour promoter described by THASTRUP et al. (Proc. Natl. Acad. Sci. (USA), 87, 2466–2470, 1990) which selectively and irreversibly inhibits the $Ca^{2+}$-ATPase of intracellular $IP_3$-sensitive $Ca^{2+}$-stores. Consequently the $Ca^{2+}$-stores are rapidly depleted. As described by J. PUTNEY (Calcium, 11, 611–624, 1990) the depletion of these stores constitutes the physiological stimulation for opening up unselective cation channels in the cell membrane. The result of this is a massive influx of $Na^+$ and $Ca^{2+}$ into the cell. Because of these properties, Thapsigargin is suitable as an indirect stimulator for agonist- and $IP_3$-independent opening up of the unselective cation channels.

Within the scope of the present invention the Thapsigargin stimulation of unselective cation channels has been carried out successfully on HL 60 cells (human leukaemia cells), on hippocampal and cortical neurone cells and on RBL-cells (rat basophilic lymphoma cells) and in this way the existence of these channels in particular cell lines was demonstrated.

The cytoplasmic $Ca^{2+}$ concentration ($[Ca^{2+}]_i$) plays an important part in the cell proliferation and in tumour growth (for a summary see L. R. ZACHARSKI, Journal of Medicine 19:145–177, 1988). In particular, the $Ca^{2+}$-influx into the cell stimulated by receptor activation with consecutive inositoltriphosphate—($IP_3$-)—mediation would appear to be of crucial importance for oncogenic cell proliferation (U. KIKKAWA and Y. NISHIZUKA, Ann. REV. CELL. BIOL. 2:149–178, 1986). This mechanism also plays a part in the formation of metastases and in "Multi-Drug Resistance". (For a summary see the above-mentioned publication by L. R. ZACHARSKI, J. MED. 19:145–177, 1980).

This hypothesis is supported by the fact that Thapsigargin, as an indirect stimulator of the unselective cation channels (UCC) not only leads to a $Ca^{2+}$-overload in the cell but is also a highly effective tumour promoter. (V. THASTRUP et al. Proceedings of the NATL. Acad. Sci: (USA) 87:2466–2470, 1990).

The blockade of the $Ca^{2+}$-influx by the UCC leads to normalisation of the intracellular Ca-ion concentration and hence to inhibition of tumour growth etc.

Conventional calcium antagonists do not inhibit these UCC. It has been found, surprisingly, that the compounds according to this invention inhibit the influx of calcium into the cell through the UCC.

As shown by S. H. MURCH et al. (Lancet 339:381–385, 15. Feb. 1992) endothelin I plays an important pathophysiological role in inflammatory intestinal diseases such as ulcerative colitis and Crohn's disease. Using immunohistochemical methods it has been shown that patients with Crohn's disease in the region of the submucosa and patients with ulcerative colitis in the region of the lamina propria of the epithelium of the large intestine show significantly and greatly increased concentrations of endothelin I compared with healthy normal people. It is assumed that the local secretion of endothelin causes massive vasospasms with consecutive disseminated ischaemia with microinfarcts which are regarded as the actual cause of the above diseases. The vasospasmogenic effectiveness of endothelin is explained by a $Ca^{2+}$-overload of vascular myocytes. Endothelin primarily triggers an $IP_3$-mediated intracellular release of $Ca^{2+}$ which is followed by a massive transmembranal $Ca^{2+}$-entry through dihydropyridine-insensitive channels. (M. S. Simonson et al. Clin. Invest. Med. 14:499–507, 1991; T. Masakai, J. Cardiovasc. Pharmacol. 13:Suppl. 5, S1–S4, 1989; D. W. Hay, R. J. Pharmacol. 100:383–392, 1990). These channels are unselective cation channels which have also been briefly described as existing in cells of the large intestine mucosa. (Chr. Siemer and H. Gögelein, Europ. J. Physiol. 420:319–328, 1992).

The endothelin-stimulated activation of fura-2-charged human leukaemia cells (HL 60 cells) has proved a suitable screening model for detecting functional endothelin antagonists. In conformity with G. GRYNKIEWICZ et al. (J. Biol. Chem. 260:3440–3450, 1985) the intracellular $Ca^{2+}$-concentration in the cytoplasm of HL 60 cells (suspensions) can be monitored by spectrofluorometry and quantified as a measurement of cell activation by endothelin. The stimulation was effected by adding 0.1 µM endothelin and could be inhibited in a dosage-dependent manner by means of the substances according to the invention.

The functional endothelin antagonism of the substances according to the invention is mediated through a blockade of the unselective cation channels. Consequently, detection of a functional Thapsigargin-antagonism on RBL-hml cells is also a suitable screening method for functional endothelin antagonists.

Carrying out the investigation:

For screening purposes, fura-2-charged adhesive RBL-hm 1 cells are stimulated with 0.1 µM Thapsigargin in a $Ca^{2+}$-free incubation medium. After 4 minutes, extracellular $Ca^{2+}$ is restored to a concentration of 1.5 mM and, using the fura-2-fluorescence, the excessive increase in the cytoplasmic $Ca^{2+}$-concentration caused by a massive transmembranal $Ca^{2+}$-entry through unselective cation channels is recorded.

This entry is to be inhibited solely by unselective cation channel blockers in a dosage-dependent manner. Neither conventional calcium antagonists nor specific blockers of agonists which stimulate the IP$_3$-turnover are able to inhibit the transmembranal Ca$^{2+}$-entry triggered indirectly by Thapsigargin. The compounds of the present invention are distinguished by their inhibition of UCC.

The fluorometric calcium measurement in the cytoplasm of individual adhering RBL-hml cells is carried out analogously to the method described by KUDO and OGURA (1986) for neuronal cells. An AXIOVERT 35 fluorescence microscope made by ZEISS is used in conjunction with an imaging system made by HAMAMATSU, consisting of the ICMS-image processing system, residual light camera with control unit and image intensifier DVS 3000.

The kinetics of the cytoplasmic Ca$^{2+}$-concentration is recorded continuously as a concentration/time curve after the cell activation stimulated by Thapsigargin (0.1 μM). The curves of two activated cell cultures are compared in the presence and absence of 10 μM test substance. The area under these curves (area under the curve=AUC) is integrated and recorded as a measurement of cell activation. The inhibitory potency of the UCC-blockers tested is determined using the following equation:

$$\% H = 100 - \frac{AUC_{inh} \times 100}{AUC_{(control)}}$$

%H=the percentage inhibition of the calcium entry through unselective cation channels which is stimulated and inhibited by 10 μM of test substance.

$AUC_{inh}$=area under the curve recorded in the presence of the stimulant plus 10 μM inhibitory test substance.

AUC control=area under the curve which is recorded only after the addition of the stimulant.

Literature relating to the above explanations:

BARNES P. J., L. W. RODGER and N. C. THOMSON Pathogenesis of asthma, in "ASTHMA, basic mechanisms and clinical management" ED by P. J. BARNES; ACADEMIC PRESS, LONDON, 1988

GRYNKIEWICZ G., M. POENIE and R. Y. TSIEN A new generation of Ca$^{2+}$-indicators with greatly improved fluorescence properties J. BIOL. CHEM. 260:3440–3450, 1985

HIDE, M. and M. A. BEAVEN Calcium influx in a rat mast cell (RBL-2H3) line J. BIOL. CHEM. 266 15221–15229, 1991

KUDO, Y. and A. OGURA Glutamate-induced increase in intracellular Ca$^{2+}$-concentration in isolated hippocampal neurones BR. J. PHARMACOL. 89:191–198; 1986

PUTNEY, J. W., jr. Capacitative Calcium entry revised CELL CALCIUM 11:611–624, 1990

RINK, T. J. Receptor-mediated calcium entry FEBS LETT. 268:381–385, 1990

SEIFERT, R. and G. SCHULTZ The superoxide forming NADPH oxidase of phagocytes: An enzyme system regulated by multiple mechanism REV. PHYSIOL. BIOCHEM. PHARMACOL., Vol. 117, SPRINGER VERL., 1991

WELLS, E., C. G. JACKSON, S. T. HARPER, J. MANN and R. P. EAOY Characterization of primate bronchoalveolar mast cells II, inhibition of histamine, LTC$_4$ and PGF$_{2\alpha}$ release from primate bronchoalveolar mast cells and a comparison with rat peritoneal mast cells J. IMMUNOL. 37:3941–3945, 1986.

Results of measurement: The percentage inhibition of UCC after Thapsigargin stimulation (0.1 μM Thapsigargin) in RBL-hm 1 cells is given. The respective concentrations of the test substances are 10$^{-5}$ mol (Table 3) or 1 μmol and 10 μmol (Table 4).

TABLE 3

RBL - hm 1 cells - Thapsigargin (0.1 μM)-stimulation

| $\diagdown$ N—R$_1$ / R$_2$ | Salt form | IC$_{50}$ | % H |
|---|---|---|---|
| NH—CH$_2$—CH(CH$_3$)$_2$ | HCl | — | 65.7 |
| NH—CH$_2$—C$_6$H$_5$ | HCl | 1.8 × 10$^{-6}$ | 90.1 |
| NH—CH$_2$—(cyclohexyl) | HCl | 2.5 × 10$^{-6}$ | 90.1 |
| N-(2-methoxyphenyl)piperazinyl | HCl | 1.77 × 10$^{-6}$ | 88.8 |
| NH—CH$_2$-(furyl) | HCl | — | 62.5 |
| NH—CH$_2$—CH$_2$-(thienyl) | HCl | 2.37 × 10$^{-6}$ | 88.4 |

TABLE 4

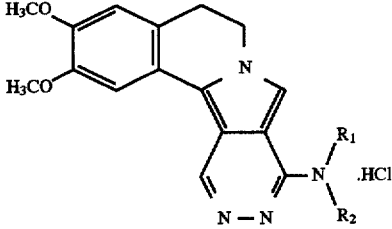

RBL - hm 1 cells - Thapsigargin (0.1 μM)-stimulation
(1) Concentration of the test substance 1 μMol
(2) Concentration of the test substance 10 μMol

| $-N\begin{matrix}R^1\\R^2\end{matrix}$ | % H 1 μM(1) | % H 10 μM(2) | IC$_{50}$ |
|---|---|---|---|
|  NH—CH$_2$CH$_2$—C$_6$H$_4$—CH$_3$ | | 95.36 | 78 × 10$^{-7}$ |
| 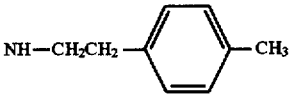 NHCH$_2$CH$_2$—C$_6$H$_5$ | 31.7 | 87.87 | |
| 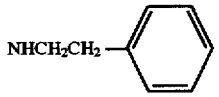 piperazinyl-(2-CN-phenyl) | 41.6 | 77.70 | |
| 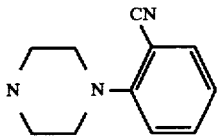 piperazinyl-(3-OCH$_3$-phenyl) | | 92.34 | 1.5 × 10$^{-6}$ |
| 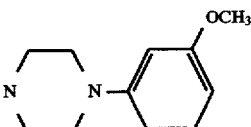 NH—CH$_2$—CH$_2$—CH$_2$—(3-CH$_3$-phenyl) | | 78.67 | |
| 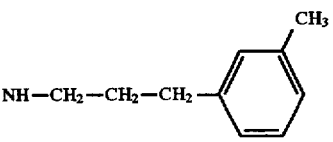 piperazinyl-(2-C$_2$H$_5$-phenyl) | 34.9 | 82.60 | |
| 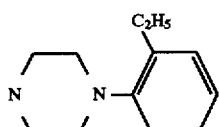 NH—CH$_2$CH$_2$—(2-F-phenyl) | 51.2 | 81.55 | 1.47 × 10$^{-6}$ |
| 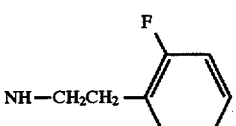 NH—CH$_2$CH$_2$—(3-CF$_3$-phenyl) | | 97.94 | 7.1 × 10$^{-7}$ |
| 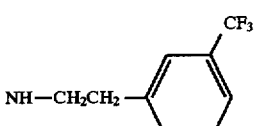 NH—CH$_2$—CH$_2$—(2-thienyl) | | 88.41 | — |

TABLE 4-continued
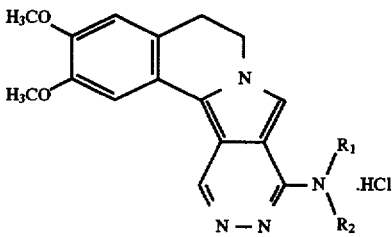
RBL - hm 1 cells - Thapsigargin (0.1 μM)-stimulation
(1) Concentration of the test substance 1 μMol
(2) Concentration of the test substance 10 μMol
| $-N\begin{matrix}R^1\\R^2\end{matrix}$ | % H 1 μM(1) | % H 10 μM(2) | IC$_{50}$ |
|---|---|---|---|
| 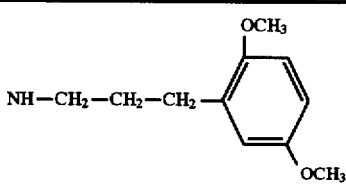 | | | |
| 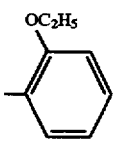 | 48.7 | 96.48 | |
| 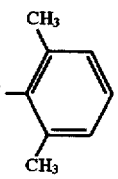 | 38.1 | 96.18 | |
| 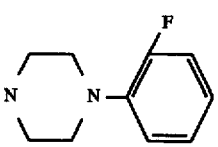 | 37.9 | 67.37 | |
|  | | 71.94 | |
| 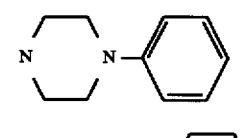 | 32.1 | 89.84 | |
|  | | 69.25 | |
| 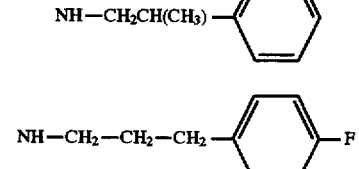 | 56.6 | 96.25 | |

TABLE 4-continued
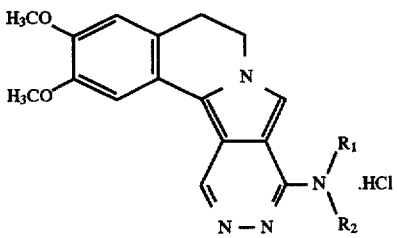
RBL - hm 1 cells - Thapsigargin (0.1 μM)-stimulation
(1) Concentration of the test substance 1 μMol
(2) Concentration of the test substance 10 μMol
| $-N\begin{matrix}R^1\\R^2\end{matrix}$ | % H 1 μM(1) | % H 10 μM(2) | IC$_{50}$ |
|---|---|---|---|
|  | 50.5 | 98.5 | |
| 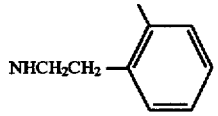 | | | |
| 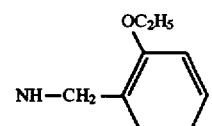 | | | |
| 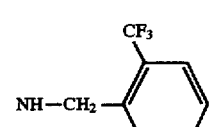 | | | |
| 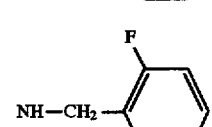 | | | |
| 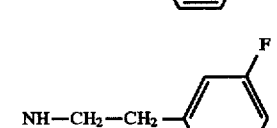 | | | |
| 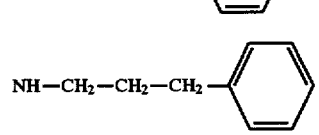 | | | |
| 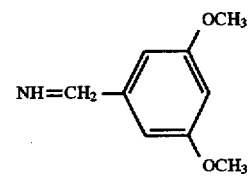 | 87.20 | | |

TABLE 4-continued
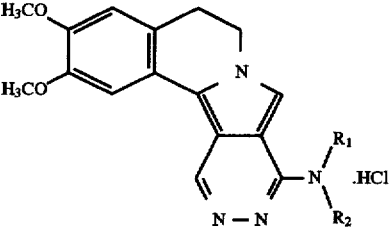
RBL - hm 1 cells - Thapsigargin (0.1 μM)-stimulation
(1) Concentration of the test substance 1 μMol
(2) Concentration of the test substance 10 μMol
| $-N\begin{smallmatrix}R^1\\R^2\end{smallmatrix}$ | % H<br>1 μM(1) | % H<br>10 μM(2) | IC$_{50}$ |
|---|---|---|---|
|  | 50.4 | 88.71 | |
| 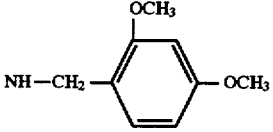 | | | |
| NH—CH$_2$—CH$_2$—CH(C$_6$H$_5$)$_2$ | 57.2 | 82.11 | |
| 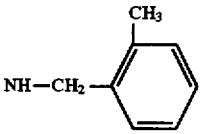 | | 56.35 | |
| 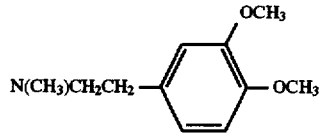 | | 48.86 | |
| NH—CH$_2$—CH$_2$—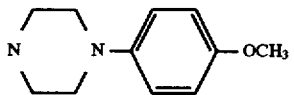 | | 98.14 | |
| 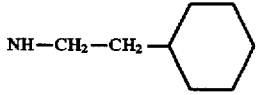 | | 60.50 | |
| 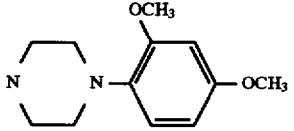 | 37.2 | 83.3 | |
| 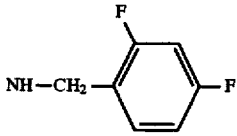 | | 62.64 | |
| NH—CH$_2$—CH(C$_6$H$_5$)$_2$ | | 35.60 | 1.43 × 10$^{-6}$ |

TABLE 4-continued
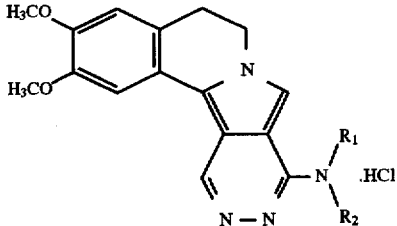
RBL - hm 1 cells - Thapsigargin (0.1 μM)-stimulation
(1) Concentration of the test substance 1 μMol
(2) Concentration of the test substance 10 μMol
| $-N\begin{matrix}R^1\\R^2\end{matrix}$ | % H 1 μM(1) | % H 10 μM(2) | IC$_{50}$ |
|---|---|---|---|
|  | | 55.84 | |
| 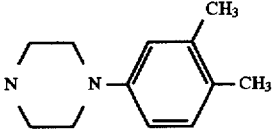 | | 99.40 | $1.43 \times 10^{-6}$ |
| 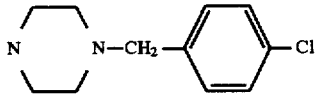 | | 71.99 | |
| 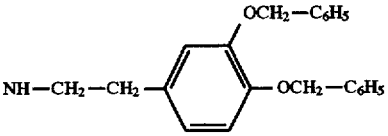 | | 58.80 | |
| 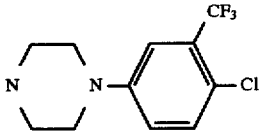 | | 84.50 | |
| 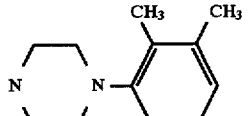 | | 91.98 | |
| 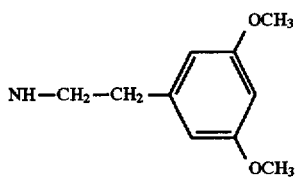 | | 75.19 | |
| 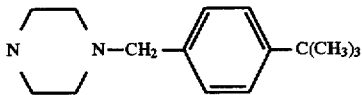 | 35.3 | 93.0 | |

TABLE 4-continued

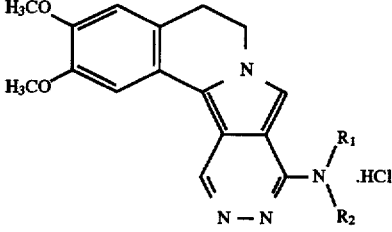

RBL - hm 1 cells - Thapsigargin (0.1 µM)-stimulation
(1) Concentration of the test substance 1 µMol
(2) Concentration of the test substance 10 µMol

| $-N\begin{matrix}R^1\\R^2\end{matrix}$ | % H<br>1 µM(1) | % H<br>10 µM(2) | IC$_{50}$ |
|---|---|---|---|
| 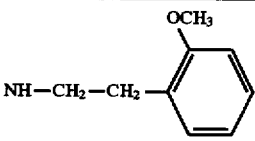 | | | |

The functional antiinflammatory effectiveness can be demonstrated by means of the following test:

Individual RBL-2H3-cells (a tumour cell line related to the mast cells) adhering to glass slides are used.

The cultivation and attachment of the RBL-2H3-cells are carried out by the method described by HIDE and BEAVEN (1991). In order to sensitise the adhesive RBL-2H3-cells the cells are incubated for 2 hours at ambient temperature with a 1:2000 diluted commercial gammaglobulin E-solution against a dinitrophenol-bovine serum albumin complex (DNP-BSA-antigen). The cells are then washed. By the addition of 0.1 ml of DNP-BSA-solution (10 µg/ml) there is a massive immunological cell activation which is mediated by a cytoplasmic $Ca^{2+}$-overload. The fluorometric calcium measurement in the cytoplasm of individual adhering RBL-2H3-cells is carried out analogously to the method described by KUDO and OGURA (1986) for neuronal cells, which is also explained hereinbefore in this specification.

The comparison used in these investigations is (10 µM) chromoglycate which brings about an approximately 50% inhibition of the antigen-induced cell activation.

In this test the above-mentioned compounds demonstrate %H values which are comparable with the values specified hereinbefore.

TABLE 5

RBL-2H3-cells: AB (monoclonal-mouse) 1:2000
Stimulation: DNP-BSA (10 µg/ml).

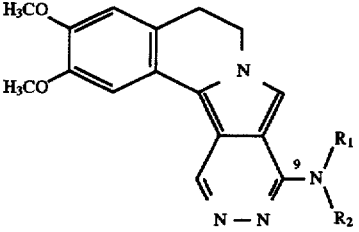

| $-N\begin{matrix}R_1\\R_2\end{matrix}$ | Salt form | % H |
|---|---|---|
| $NH-CH_2-CH(CH_3)_2$ | HCl | 41.4 |
| $NH-CH_2-C_6H_5$ | BS | 97.9 |
| 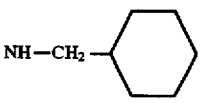 | HCl | 95.4 |
| 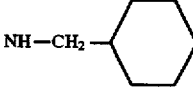 | HCl | 82.0 |
| 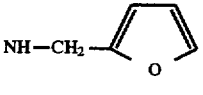 | HCl | 54.4 |
| 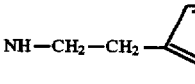 | HCl | 65.8 |

TABLE 5-continued

RBL-2H3-cells: AB (monoclonal-mouse) 1:2000
Stimulation: DNP-BSA (10 μg/ml).

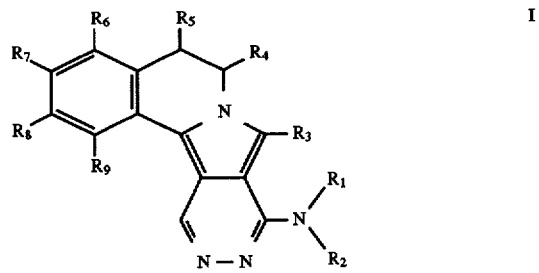

| | Salt form | % H |
|---|---|---|
| Fenoterol | | 38.5 |
| Na-Chromo. | | 9.0 |

Tests on microcultures of various human tumour cell lines using the tetrazolium assay in order to determine the antiproliferative effect of the substances according to the invention surprisingly showed that the compound tested was 5 to 100 times more potent than the comparison substance Verapamil.

The antiproliferative effectiveness of the test substances was determined by means of the MTT test described by MOSMANN (J. IMMUNOL. METH. 65:55–63, 1983), DENIZOT et al. (J. IMMUNOL. METH. 89:271–277, 1986) and J. ELIASON et al. (INT. J. CANCER 46:113–117, 1990). (MTT=[3-(4,5-dimethylthiazol-2-yl)2,5-diphenyltetrazolium bromide] produced by CHEMICON Inc. El Segundo, Calif., USA). This indicator is metabolised only by living cells with intact mitochondria into a blue formazane product. The following human tumour cell lines were used in our test: A 549 (adenocarcinoma of the lung), A 431 (epidermal carcinoma of the vulva), PC 3 (adenocarcinoma of the prostate), SK BR 3 (adenocarcinoma of the breast), HT 29 (CX1 1) (adenocarcinoma of the colon) and K 562 (chronic myeloid leukaemia cell). The test was carried out on microtiter plates. Each well contained 100 μl of a cell suspension (0.2×10$^6$ cells per ml). The incubation medium used was RPMI 1640 with 10% heat-inactivated foetal calves' serum and 50 μg/ml of gentamycin. The cell suspensions were incubated for 0, 24, 48 or 72 hours in air with a humidity at saturation point in a $CO_2$ (5%)/air (95%) mixture at 37° C., incubated in the presence and absence of variable concentrations of antiproliferative test substances. The test substances were dissolved in DMSO (final dilution: 0.1%). Then 10 μl of MTT-solution (3 mg/ml) were added, followed after 3 hours by 100 μl of an isopropanol solution containing 0.08N HCl. After a further hour, the light absorption at 570 nm (comparative wavelength 630 nm) was determined in a microplate reader. The light absorption is directly proportional to the number of living cells. The half-maximum inhibitory concentrations of the substances tested were 1 μg/ml.

The vasospasmolytic effectiveness of the above-mentioned functional endothelin and Thapsigargin antagonists were confirmed on an isolated blood vessel preparation: coronary perfusion was continuously quantified, on retrogressively perfused, spontaneously beating LANGENDORFF hearts taken from rats, by means of electromagnetic flow measurement (apparatus supplied by Hugo Sachs Elektronik, MARCH). This measuring apparatus could be used to record the extent, duration and pattern of vascular spasms with a high degree of accuracy. If perfusion is carried out with 100 nM endothelin concentration, the coronary perfusion flow is reduced from 11 to 5 ml/min. The restriction in perfusion can be reversed by means of the substances according to the invention. The potencies of the compounds according to the invention with regard to Thapsigargin inhibition on fura-2-charged RBL-hml-cells or the effectiveness of endothelin-inhibition on fura-2-charged HL 60 cells correlates clearly with the vasospasmolytic effectiveness of the test substances detected on the Langendorff preparation. It can be concluded from this that, underlying the vasospasmolytic endothelin antagonism of the substances tested, there is a blockade of the unselective cation channels.

According to a further aspect of the invention are provided compounds of general formula I

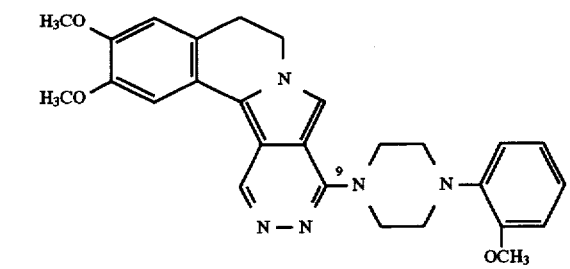

wherein $R_3$, $R_4$, $R_5$, $R_6$ and $R_9$ denote hydrogen, $R_7$ and $R_8$ denote $C_{1-4}$-alkoxy or $R_7$ and $R_8$ together represent —$OCH_2O$— or —$OCH_2CH_2O$—, and the group $NR_1R_2$ represents

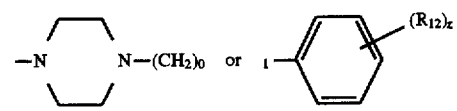

wherein z is zero, 1 or 2 and $R_{12}$ is CN, $CF_3$, halogen, $(C_{1-4})$alkyl or $(C_{1-4})$alkoxy, with the exception of the compound

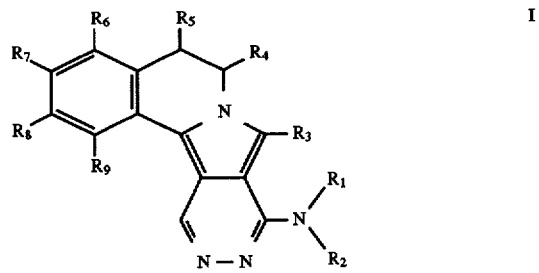

Preferred are compounds of formula I as defined above in which $R_7$ and $R_8$ represent methoxy.

Also preferred are compounds of formula I wherein $R_{12}$ is CN, $OCH_3$, $CH_3$, $C_2H_5$, $C(CH_3)_3$, F, Cl or $CF_3$.

Further preferred are compounds of formula I wherein —$NR_1R_2$ is the group

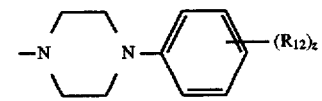

wherein $R_{12}$ and z are defined as above.

Particularly preferred compounds of formula I are those wherein $R_7$ and $R_8$ are methoxy and —$NR_1R_2$ represents one of the following groups:

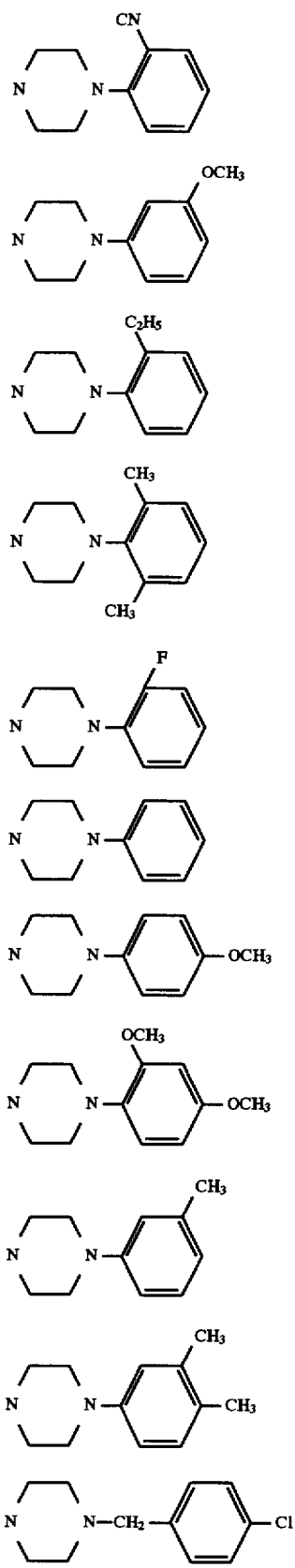

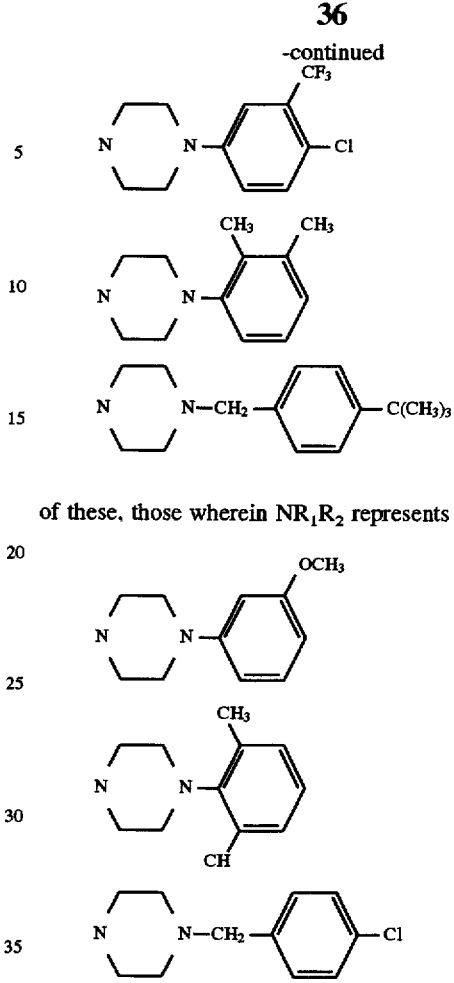

of these, those wherein $NR_1R_2$ represents

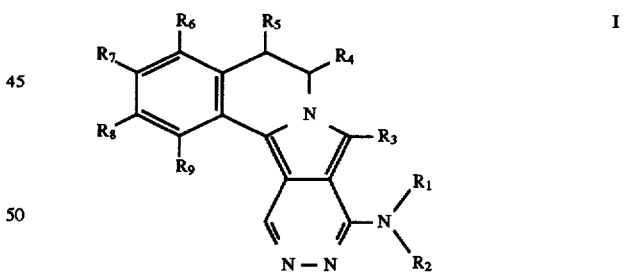

are particularly preferred.

According to a yet further aspect of the invention, we provide compounds of general formula I

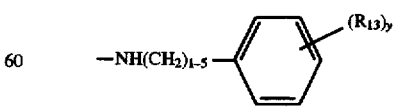

wherein $R_3$, $R_4$, $R_5$, $R_6$ and $R_9$ denote hydrogen, $R_7$ and $R_8$ denote $C_{1-4}$-alkoxy or $R_7$ and $R_8$ together denote —$OCH_2O$— or —$OCH_2CH_2O$— and the group —$NR_1R_2$ denotes —NH(CH$_2$)$_{1-5}$—⬡—(R$_{13}$)$_y$ or —$NH(CH_2)_{1\ or\ 2}CH(C_6H_5)_2$, wherein $R_{13}$ is $CF_3$, $C(CH_3)_3$ or —$OCH_2C_6H_5$ and y represents 1 or 2.

Preferred compounds of formula I as defined above are those wherein —$NR_1R_2$ represents the group

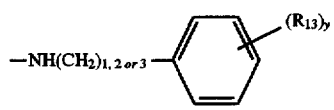

wherein $R_{13}$ and y are defined as above.

Also preferred are compounds of formula I as defined above wherein $R_7$ and $R_8$ represent methoxy.

Further preferred are those compounds of formula I defined above, wherein $R_7$ and $R_8$ denote methoxy and —$NR_1R_2$ has one of the following meanings:

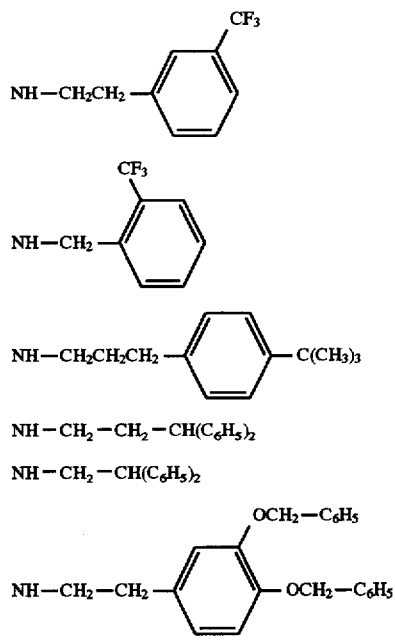

According to a yet further aspect of the invention we provide compounds of general formula I

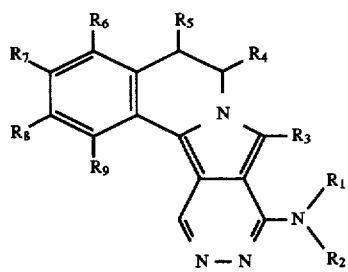

wherein $R_3$, $R_4$, $R_5$, $R_6$ and $R_9$ represent hydrogen, $R_7$ and $R_8$ represent methoxy and —$NR_1R_2$ has one of the following meanings:

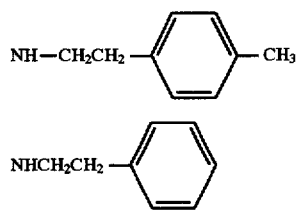

-continued

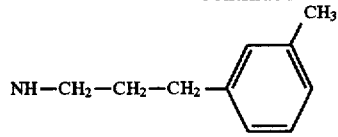

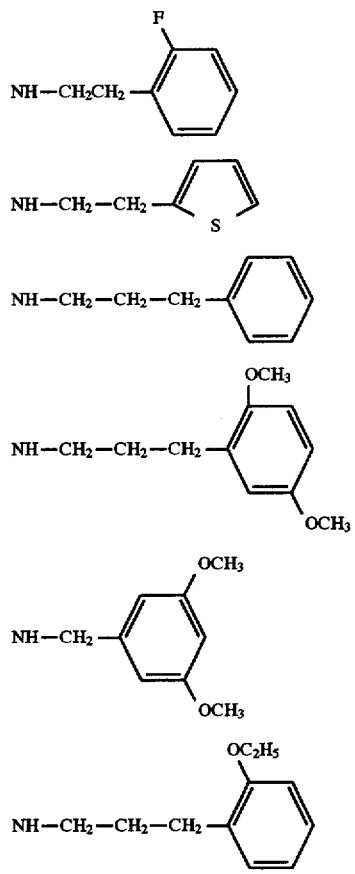

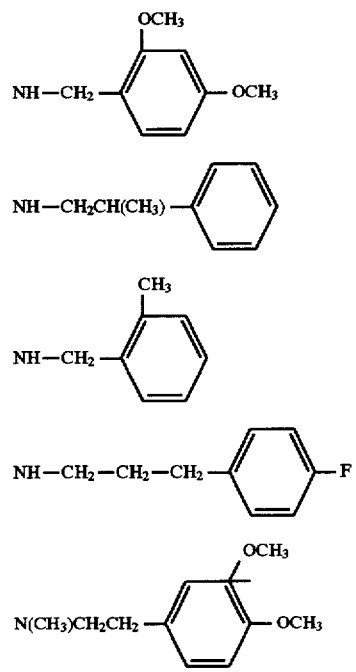

-continued
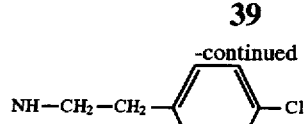
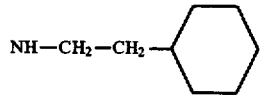
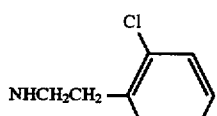
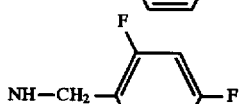
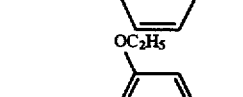
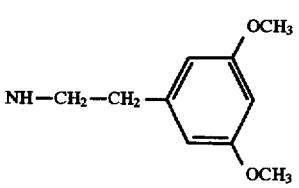
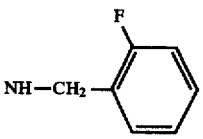
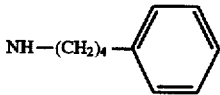
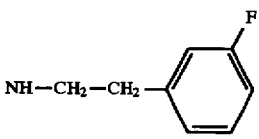
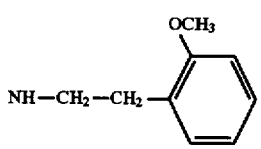
of which, compounds wherein —NR$_1$R$_2$ has one of the following meanings:
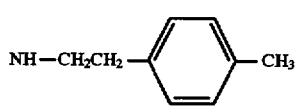
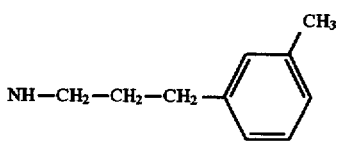
-continued
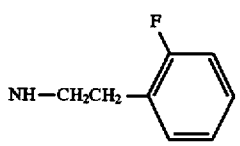
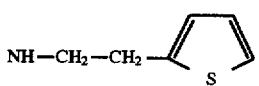
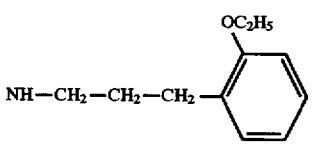
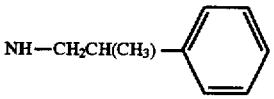
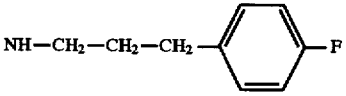
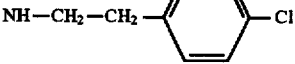
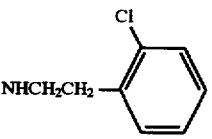
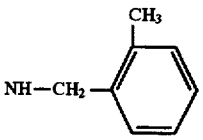
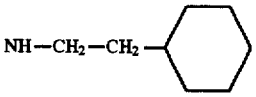
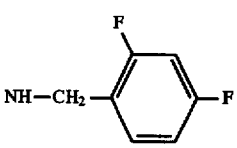
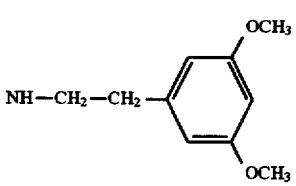
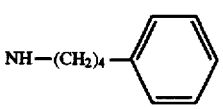

preferably 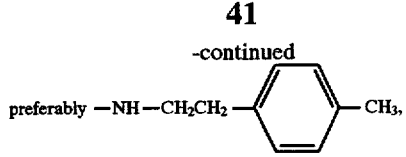

are particularly preferred.

The invention also comprises the physiologically acceptable salts of the above-defined compounds of formula I with acids, bases or complexing agents.

The compounds may be administered both enterally and parenterally. The suggested dose for oral use ranges from 0.1 to 500 mg of active substance per dose and, for intravenous use, from 0.05 to 150 mg per dose. The desired therapeutic dose depends on the indication and form of administration and can be determined experimentally.

Suitable forms include, for example, tablets, capsules, suppositories, solutions, syrups, emulsions, aerosols or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxypolymethylene, carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellack, gum arabic, talc, titanium dioxide or sugar. In order to obtain delayed release or avoid incompatibilities, the core may also consist of several layers. Similarly, the tablet coating may consist of several layers to achieve delayed release, whilst the excipients mentioned for the tablets may be used.

Syrups containing the active substances or combinations of active substances according to the invention additionally contain a sweetener such as saccharin, cyclamate, glycerol or sugar as well as a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene diamine tetraacetic acid, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

Processes for preparing the compounds of formula Ia are described in European Patent Applications 190 563 and 252 299, to which reference is hereby made.

The new compounds may be obtained by a variety of methods but one convenient method involves reacting a compound of general formula II

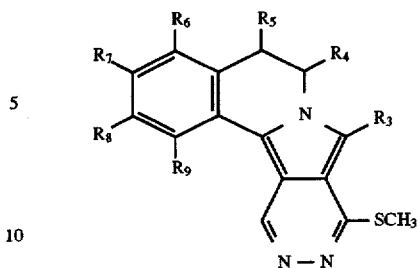

wherein the groups $R_3$, $R_4$, $R_5$, $R_6$, $R_7$, $R_8$ and $R_9$ are as hereinbefore defined, with a compound of general formula III

wherein $R_1$ and $R_2$ are as hereinbefore defined, followed by formation of any salts with acids, bases or complex forming agents as desired.

A starting compound of general formula II is dissolved in a high boiling inert solvent, e.g. dimethylformamide, dimethylacetamide, chlorobenzene or hexamethylphosphoric acid triamide and refluxed with the amine component of general formula III until the reaction has ended. The reaction time is between 1 and 15 hours and depends on the starting components used.

In the case of reactive amines, it is also possible to use alcohols or tetrahydrofuran as solvent; under some circumstances it may be advantageous to carry out the reaction in an autoclave.

If the amines used are liquid and sufficiently high boiling, the reaction can also be carried out in an excess of the amine without any additional solvent (e.g. with aniline, morpholine, phenylethylamine), optionally under a nitrogen atmosphere.

In some cases it is also possible to use a reactant which acts as a solvent during the reaction and also yields the desired amine, e.g. dimethylformamide, by cleaving during the reaction.

The 9-amino-pyridazino-pyrazolo-isoquinolines according to the invention are bases and may be converted into any desired physiologically harmless acid addition salts with organic or inorganic acids in the usual way.

Acids suitable for salt formation include for example inorganic acids, such as hydrochloric acid, hydrobromic acid, hydriodic acid, hydrofluoric acid, sulphuric acid, phosphoric acid and nitric acid, and organic acids such as acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid and methanesulphonic acid.

The following Examples illustrate aspects of the invention:

EXAMPLES 5,6-Dihydro-2,3-dimethoxy-9-4-[(2,6-dimethyl)-piperazino]-pyridazino[4',5':3,4]pyrrolo[2,1-a]-isoquinoline-hydrochloride.

3 g of S-methyl compound (hydrochloride), 5 ml of 1-(2,6-dimethylphenyl)-piperazine and 50 ml of toluene are refluxed for about 5 hours. After the reaction has ended (monitored by TLC) the mixture is cooled and the reaction product is suction filtered.

It is washed twice with toluene and divided between $CH_2Cl_2$ and dilute NaOH. The organic phase is washed several times with water, dried over $Na_2SO_4$ and concentrated by evaporation. The residue is taken up in a little $CH_2Cl_2$, optionally after purification over a silica gel column (eluant $CH_2Cl_2$/NaOH=100+10 V.V.) and converted into the hydrochloride by the addition of ethanolic HCl. Yield 2.86 g (68% of theory), melting point: 294°–295° C.

Pharmaceutical Examples a) Coated tablets 1 tablet core contains:

| | |
|---|---|
| Active substance of general formula Ia | 30.0 mg |
| Lactose | 100.0 mg |
| Corn starch | 75.0 mg |
| Gelatine | 3.0 mg |
| Magnesium stearate | 2.0 mg |
| | 210.0 mg |

Preparation

The active substance mixed with lactose and corn starch is granulated with a 10% aqueous gelatine solution through a 1 mm mesh screen, dried at 40° C. and rubbed through a screen once more. The granules thus obtained are mixed with magnesium stearate and compressed. The cores produced in this way are coated in the usual manner with a coating consisting of an aqueous suspension of sugar, titanium dioxide, talc and gum arabic. The finished coated tablets are polished with beeswax.

b) Tablets

| | |
|---|---|
| Active substance of general formula Ia | 30.0 mg |
| Lactose | 100.0 mg |
| Corn starch | 70.0 mg |
| Soluble starch | 7.0 mg |
| Magnesium stearate | 3.0 mg |
| | 210.0 mg |

Preparation

The active substance and magnesium stearate are granulated with an aqueous solution of the soluble starch, the granules are dried and intimately mixed with lactose and corn starch. The mixture is then compressed into tablets weighing 210 mg.

c) Capsules

| | |
|---|---|
| Active substance according to claim 18 | 20.0 mg |
| Lactose | 230.0 mg |
| Corn starch | 40.0 mg |
| Talc | 10.0 mg |
| | 300.0 mg |

Preparation

The active substance, lactose and corn starch are first combined in a mixer and then in a grinding machine. The mixture is returned to the mixer, thoroughly combined with the talc and mechanically packed into hard gelatine capsules.

We claim:

1. Compounds of general formula I

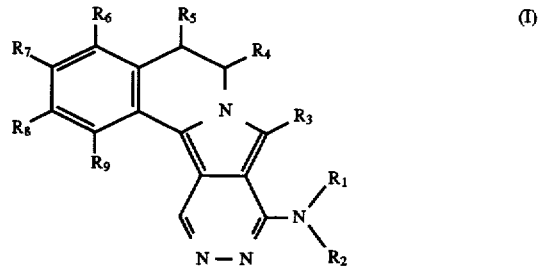

wherein $R_3$, $R_4$, $R_5$, $R_6$ and $R_9$ denote hydrogen, $R_7$ and $R_8$ denote $C_{1-4}$-alkoxy or $R_7$ and $R_8$ together represent —$OCH_2O$— or —$OCH_2CH_2O$—, and the group $NR_1R_2$ represents

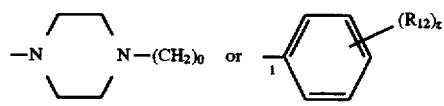

wherein z is zero, 1 or 2 and $R_{12}$ is CN, $CF_3$, halogen, $(C_{1-4})$alkyl or $(C_{1-4})$alkoxy, or the physiologically acceptable salts thereof with acids, bases or complexing agents, with the exception of the compound

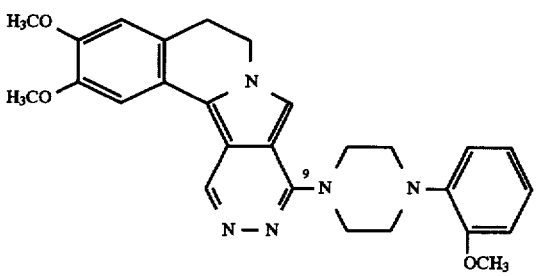

2. Compounds according to claim 1, wherein $R_7$ and $R_8$ represent methoxy.

3. Compounds according to claim 1 or 2, wherein $R_{12}$ is CN, $OCH_3$, $CH_3$, $C_2H_5$, $C(CH_3)_3$, F, Cl or $CF_3$.

4. Compounds according to one of claims 1 to 3, wherein —$NR_1R_2$ is the group

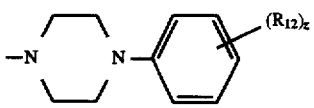

wherein $R_{12}$ and z are defined as in one of claims 1 to 3.

5. Compounds according to claim 1, wherein $R_7$ and $R_8$ are methoxy and —$NR_1R_2$ represents one of the following groups:

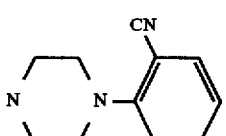

-continued

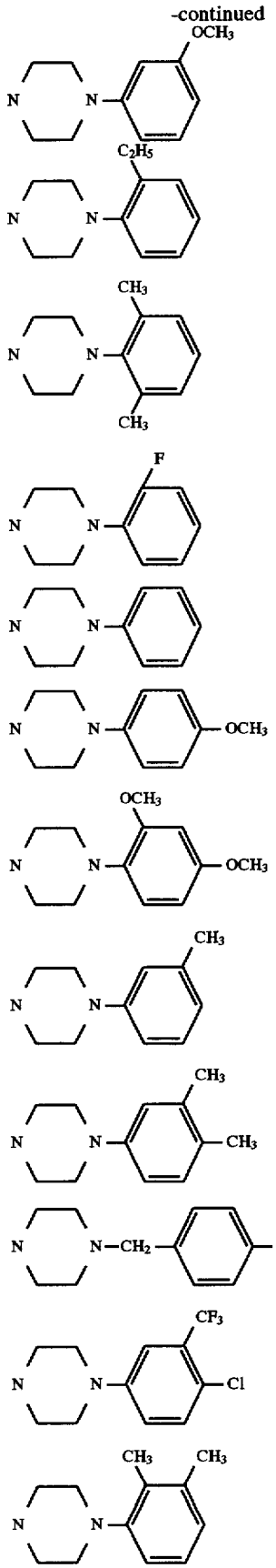

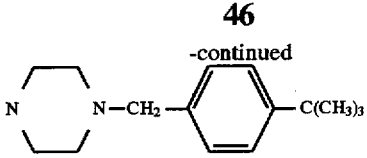

6. Compounds according to claim 5 wherein $NR_1R_2$ represents

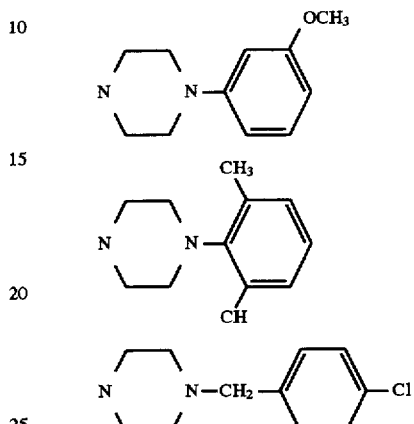

7. Compounds of general formula I

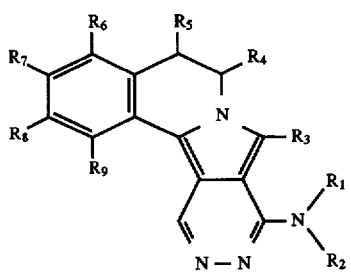

wherein $R_3$, $R_4$, $R_5$, $R_6$ and $R_9$ denote hydrogen, $R_7$ and $R_8$ denote $C_{1-4}$-alkoxy or $R_7$ and $R_8$ together denote —$OCH_2O$— or —$OCH_2CH_2O$— and the group —$NR_1R_2$ denotes

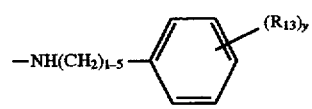

or —NH(CH$_2$)$_{1\ or\ 2}$CH(C$_6$H$_5$)$_2$, wherein $R_{13}$ is $CF_3$, $C(CH_3)_3$ or —$OCH_2C_6H_5$ and y represents 1 or 2, or the physiologically acceptable salts thereof with acids, bases or complexing agents.

8. Compounds according to claim 7, wherein —$NR_1R_2$ represents the group

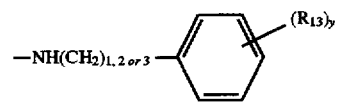

wherein $R_{13}$ and y are defined as in claim 7.

9. Compound according to one of claims 7 to 8, wherein $R_7$ and $R_8$ represent methoxy.

10. Compound according to claim 7, wherein $R_7$ and $R_8$ denote methoxy and —$NR_1R_2$ has one of the following meanings:

11. Compound of general formula I
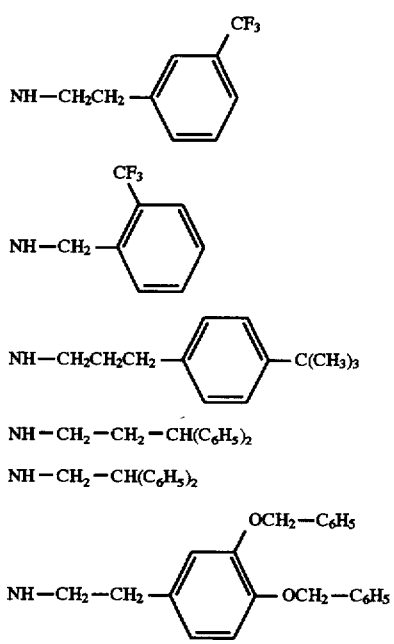
wherein $R_3$, $R_4$, $R_5$, $R_6$ and $R_9$ represent hydrogen, $R_7$ and $R_8$ represent methoxy and —$NR_1R_2$ has one of the following meanings:

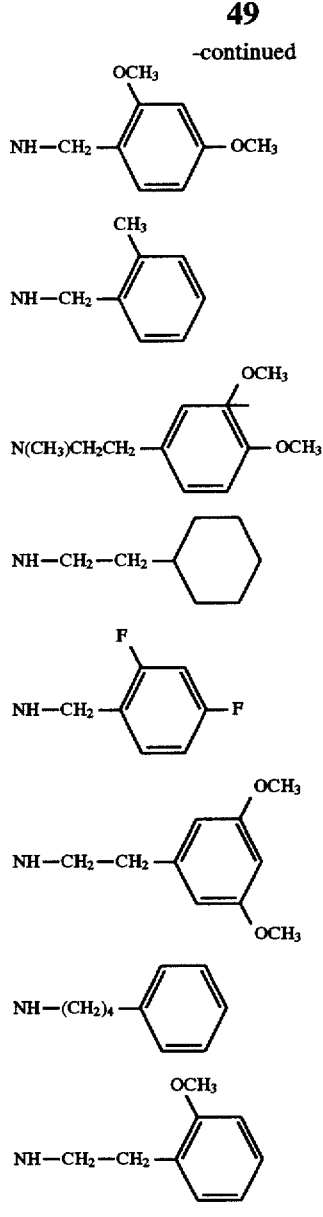

or the physiologically acceptable salts thereof with acids, bases or complexing agents.

12. Compound according to claim 11, wherein —NR₁R₂ has one of the following meanings:

preferably

13. Process for preparing compounds of general formula I according to one of claims 1 to 12 or physiologically acceptable salts thereof with acids, bases or complexing agents, in which a compound of general formula II

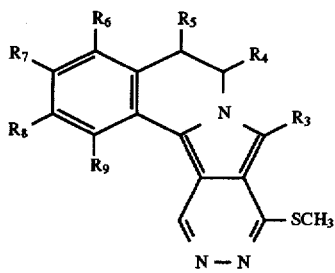

wherein the groups $R_3$, $R_4$, $R_5$, $R_6$, $R_7$, $R_8$ and $R_9$ are as hereinbefore defined, is reacted with a compound of general formula

wherein $R_1$ and $R_2$ are as hereinbefore defined, and an end product thus obtained is optionally converted into a physiologically acceptable salt in a manner known per se.

14. A process as claimed in claim 13 substantially as hereinbefore described.

15. A compound of formula (I) as defined in claim 1 whenever prepared by a process as claimed in either of claims 13 and 14.

16. Pharmaceutical preparations containing as active substance one or more compounds according to any one of claims 1 to 12 or 15 in conjunction with conventional diluents, excipients or carriers.

17. Process for producing pharmaceutical preparations according to claim 16, characterised in that compounds according to any one of claims 1 to 12 or 15 are processed with conventional galenic excipients diluents and/or carriers to form pharmaceutical preparations.

18. Use of compounds of formula (Ia)

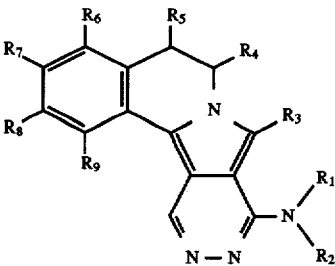

wherein $R_1$ and $R_2$, which may be identical or different, denote hydrogen; $C_{3-7}$-cycloalkyl; $C_{2-5}$-alkenyl; phenyl (wherein the phenyl ring may optionally be mono- or disubstituted by halogen or methoxy); propargyl; a straight-chained or branched, saturated or unsaturated $C_{1-5}$-alkyl, which may be substituted by hydroxy, $C_{1-4}$-alkoxy, halogen, $NH_2$, NH-alkyl having 1 to 2 carbon atoms, N,N-di($C_{1-2}$)alkylamino, NH-acyl having 2 to 4 carbon atoms, $C_{3-7}$-cycloalkyl, 1 or 2 phenyl groups, wherein the phenyl ring or rings may in turn be mono- or disubstituted by halogen, $CF_3$, $C_{1-4}$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms, alkylsulphonylamino or benzyloxy), furyl, thienyl, a nitrogen-containing heterocyclic 5- or 6-membered ring which may optionally contain as further heteroatom an oxygen or sulphur atom (whilst the ring may optionally be substituted by $C_{1-4}$-alkyl); or $R_1$ and $R_2$ together with the nitrogen atom denote a 3- to 7-membered ring which may optionally contain, as a further heteroatom, an oxygen or nitrogen atom, whilst this ring is optionally substituted by phenyl-($C_{0-4}$)-alkyl (whilst the phenyl ring may in turn be mono- or disubstituted by halogen, $CF_3$, ($C_{1-4}$)alkoxy, ($C_{1-4}$) alkyl or CN, whilst the substituents may be identical or different); or if $R_1$ denotes hydrogen, $R_2$ may also represent $-NH_2$; di($C_{1-2}$)alkylamino; acetonylamino; $-NH(C_{2-3})$acyl; an alkylsulphonyl or alkoxycarbonyl group having 1 to 3 carbon atoms in the alkyl chain; the isopropylideneamino group

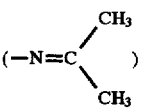

or a heterocyclic 5- or 6-membered ring containing a nitrogen atom and optionally an oxygen, nitrogen or sulphur atom as a further heteroatom;

$R_3$, $R_4$ and $R_5$, which may be identical or different denote hydrogen or a $C_{1-4}$-alkyl group;

$R_7$ and $R_8$, which may be identical or different, represent hydroxy; $C_{1-4}$-alkoxy; or $C_{1-4}$-alkylthio and $R_6$ and $R_9$, which may be identical or different, denote hydrogen; hydroxy; $C_{1-4}$-alkoxy; $C_{1-4}$-alkylthio; or the group

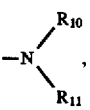

wherein $R_{10}$ denotes hydrogen; or $C_{1-4}$-alkyl and $R_{11}$ denotes hydrogen; or $C_{1-4}$-alkyl, whilst the alkyl group may optionally be substituted by hydroxy, methoxy or furfuryl;

or 2 adjacent substituents of the substituents $R_6$, $R_7$, $R_8$ and $R_9$ together form the group $-O-(CH_2)_1$ or $_2-O-$ and the other two substituents are as hereinbefore defined;

and the physiologically acceptable salts thereof with acids, bases or complexing agents for preparing agents for treating chronic inflammatory processes, ulcerative colitis and Crohn's disease, and for preparing agents having an antiproliferative activity.

19. Use of a compound of formula (Ia) according to claim 18, wherein $R_1$ and $R_2$, which may be identical or different, represent hydrogen; $C_{3-7}$-cycloalkyl; $C_{2-5}$-alkenyl; phenyl (wherein the phenyl ring is optionally mono- or disubstituted by halogen or methoxy); propargyl; a straight-chained or branched, saturated or unsaturated $C_{1-5}$-alkyl group which may be substituted by hydroxy, $C_{1-4}$-alkoxy, halogen, $NH_2$, NH-alkyl having 1 to 2 carbon atoms, N,N-di($C_{1-2}$)alkylamino, NH-acyl having 2 to 4 carbon atoms, $C_{3-7}$-cycloalkyl, phenyl (whilst the phenyl ring may in turn be mono- or disubstituted by halogen, $C_{1-2}$-alkyl, $C_{1-2}$-alkoxy, NH-alkyl having 1 to 2 carbon atoms, N,N-dialkyl having 1 to 2 carbon atoms, NH$_2$, N-acyl having 2 to 3 carbon atoms or alkylsulphonylamino), furyl, thienyl, a nitrogen-containing heterocyclic 5- or 6-membered ring which may optionally contain an oxygen or sulphur atom as a further heteroatom (whilst the ring is optionally substituted by C$_{1-4}$-alkyl); or R$_1$ and R$_2$ together with the nitrogen atom denote a 3- to 7-membered ring which may optionally contain an oxygen or nitrogen atom as a further heteroatom, whilst this ring is optionally substituted by phenyl-(C$_{0-4}$)alkyl (whilst the phenyl ring is in turn mono- or disubstituted by halogen or methoxy); or R$_2$, if R$_1$ denotes hydrogen, may also denote —NH$_2$; di(C$_{1-2}$)alkylamino; acetonylamino; —NH(C$_{2-3}$)acyl; an alkylsulphonyl or alkoxycarbonyl group each having 1 to 3 carbon atoms in the alkyl chain; the isopropylideneamino group

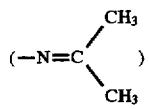

or a heterocyclic 5- or 6-membered ring containing a nitrogen atom and optionally, as a further heteroatom, an oxygen, nitrogen or sulphur atom;

R$_3$, R$_4$ and R$_5$, which may be identical or different, denote hydrogen or a C$_{1-4}$-alkyl group;

R$_7$ and R$_8$, which may be identical or different, denote hydroxy; C$_{1-4}$-alkoxy; or C$_{1-4}$-alkylthio and R$_6$ and R$_9$, which may be identical or different, denote hydrogen; hydroxy; C$_{1-4}$-alkoxy; C$_{1-4}$-alkylthio; or the group

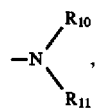

wherein R$_{10}$ denotes hydrogen; or C$_{1-4}$-alkyl and R$_{11}$ denotes hydrogen; or C$_{1-4}$-alkyl, whilst the alkyl group may optionally be substituted by hydroxy, methoxy or furfuryl;

and the physiologically acceptable salts thereof with acids, bases or complexing agents for preparing agents for treating chronic inflammatory processes, ulcerative colitis and Crohn's disease, and for producing agents with an antiproliferative activity.

20. Use of a compound according to claim 19 wherein —NR$_1$R$_2$ represents

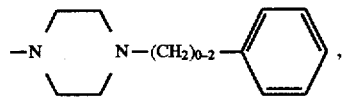

wherein the phenyl group may be substituted by one or two methoxy groups.

21. Use of a compound according to one of claims 18 to 20, wherein

—NR$_1$R$_2$ denotes the group

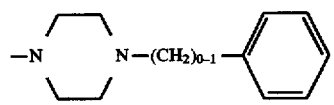

wherein the phenyl group may be substituted as in any of claims 18, 19 or 20.

22. Use of a compound according to claim 18 or 19, wherein —NR$_1$R$_2$ denotes the group

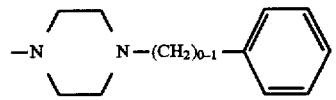

wherein the phenyl ring is mono- or disubstituted by fluorine, chlorine, CF$_3$, methoxy, methyl, ethyl or CN.

23. Use of a compound according to claim 18 or 19, wherein R$_1$ is hydrogen and R$_2$ is a straight-chained or branched C$_{1-4}$-alkyl group which is substituted by C$_{3-7}$-cycloalkyl, thienyl or 1 or 2 unsubstituted phenyl groups or a substituted phenyl group the substituent(s) of which is or are defined as in claim 18 or 19.

24. Use of a compound according to claim 23, wherein R$_1$ is hydrogen and R$_2$ is (C$_{1-4}$)alkylcyclohexyl, preferably —CH$_2$-C$_6$H$_{11}$.

25. Use of a compound according to claim 23, wherein R$_1$ is hydrogen and R$_2$ is (C$_{1-4}$)alkylphenyl, wherein the phenyl group is unsubstituted or mono- or disubstituted by F, Cl, CF$_3$, methyl, ethyl, methoxy or ethoxy.

26. Use of a compound according to claim 18 or 19, wherein NR$_1$R$_2$ is one of the following groups:

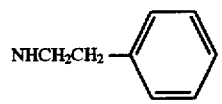

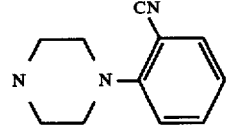

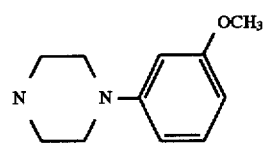

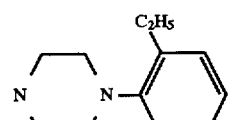

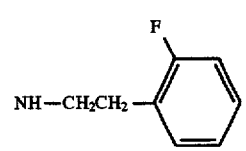

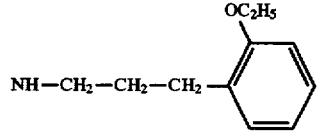
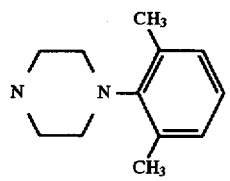
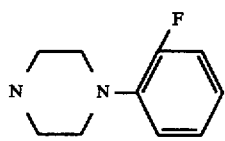
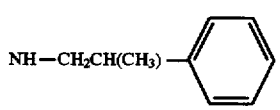
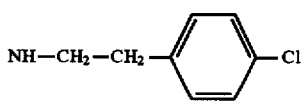
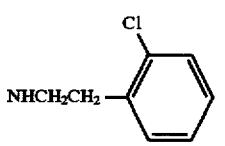
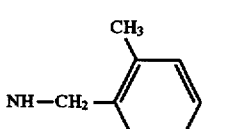
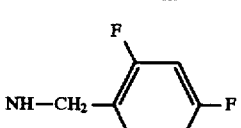
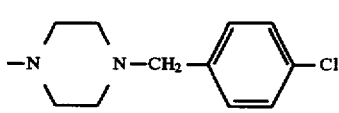
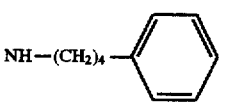
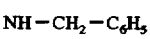
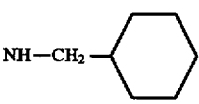
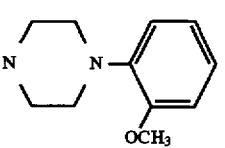

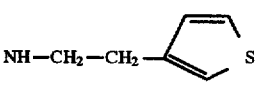
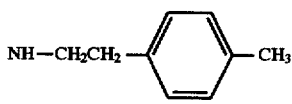
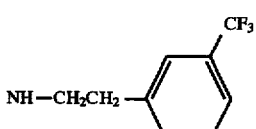

27. Use of a compound according to claim 26 wherein $NR_1R_2$ is one of the following groups:

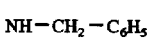
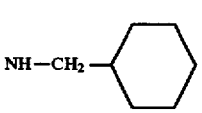
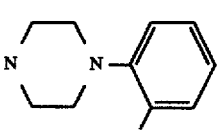
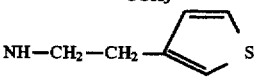
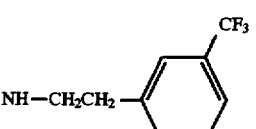
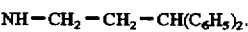

28. Use of a compound according to one of claims 18 to 27, wherein $R_3$, $R_4$, $R_5$, $R_6$ and $R_9$ denote hydrogen and $R_7$ and $R_8$ represent $C_{1-4}$-alkoxy or $R_7$ and $R_8$ together represent —$OCH_2O$— or —$OCH_2CH_2O$—.

29. Use of a compound according to claim 28 wherein $R_7$ and $R_8$ are methoxy.

30. A method of treating chronic inflammatory processes, ulcerative colitis, Crohn's disease and conditions requiring antiproliferative activity, which comprises administering to a human or animal subject an effective amount of a compound of formula (Ia) as defined in any one of claims 18 to 29.

* * * * *